(12) United States Patent
Chang et al.

(10) Patent No.: US 7,989,597 B2
(45) Date of Patent: Aug. 2, 2011

(54) IMMUNOGENIC MEMAPSIN 2 β-SECRETASE PEPTIDES AND METHODS OF USE

(75) Inventors: Wan-Pin Chang, Edmond, OK (US); Jordan Tang, Edmond, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 74 days.

(21) Appl. No.: 12/489,314

(22) Filed: Jun. 22, 2009

(65) Prior Publication Data

US 2010/0015154 A1    Jan. 21, 2010

Related U.S. Application Data

(60) Provisional application No. 61/074,468, filed on Jun. 20, 2008.

(51) Int. Cl.
C07K 16/00 (2006.01)
C12P 21/08 (2006.01)
A61K 39/395 (2006.01)

(52) U.S. Cl. ........... 530/388.26; 530/388.1; 530/388.15; 530/387.1; 424/130.1; 424/141.1; 424/142.1; 424/146.1

(58) Field of Classification Search .................. None
See application file for complete search history.

(56) References Cited

U.S. PATENT DOCUMENTS

| | | | |
|---|---|---|---|
| 6,545,127 B1 | 4/2003 | Tang et al. | 530/350 |
| 6,790,610 B2 * | 9/2004 | Gurney et al. | 435/4 |

FOREIGN PATENT DOCUMENTS

| | | |
|---|---|---|
| WO | WO 2007/021886 | 2/2007 |
| WO | WO 2009/121948 | 10/2009 |

OTHER PUBLICATIONS

Capell et al., "Maturation and pro-peptide cleavage of beta-secretase," *J. Biol. Chem.*, 275:30849-30854, 2000.
Chang et al., "Amyloid-beta reduction by memapsin 2 (beta-secretase) immunization," *FASEB J.*, 21:3184-3196, 2007.
Chang et al., "P2-323: Memapsin 2 (beta-secretase, BACE) immunization as specific and safe therapy for Alzheimer's disease," *Alzheimer's & Dementia: Journal of the Alzheimer's Association*, 4: T467, 2008.
Ermolieff et al., "Proteolytic activation of recombinant pro-memapsin 2 (pro-beta-secretase) studied with new fluorogenic substrates," *Biochemistry*, 39:12450-12456, 2000.
Harada et al., "Beta-site APP cleaving enzyme 1 (BACE1) is increased in remaining neurons in Alzheimer's disease brains," *Neuroscience Research*, 54:24-29, 2006.
He et al., "Memapsin 2 (beta-secretase) cytosolic domain binds to the VHS domains of GGA1 and GGA2: implications on the endocytosis mechanism of memapsin 2," *FEBS Lett.*, 524:183-187, 2002.
Hong et al., "Structure of the protease domain of memapsin 2 (beta-secretase) complexed with inhibitor," *Science*, 290:150-153, 2000.
Hussain et al., "Identification of a novel aspartic protease (Asp 2) as beta-secretase," *Mol. Cell. Neurosci.*, 14:419-427, 1999.
International Search Report and Written Opinion, issued in Application No. PCT/US2009/048176, date of mailing Nov. 12, 2009.
Lin et al., "Human aspartic protease memapsin 2 cleaves the beta-secretase site of beta-amyloid precursor protein," *Proc. Natl. Acad. Sci. U.S.A.*, 97:1456-1460, 2000.
Oddo et al., "Temporal profile of amyloid-beta (Abeta) oligomerization in an in vivo model of Alzheimer disease. A link between Abeta and tau pathology," *J. Biol. Chem.*, 281:1599-1604, 2006.
Sinha et al., "Purification and cloning of amyloid precursor β-secretase from human brain," *Nature*, 402:537-540, 1999.
Turner et al., "Subsite specificity of memapsin 2 (beta-secretase): implications for inhibitor design," *Biochemistry*, 40:10001-10006, 2001.
Vassar et al., "Beta-secretase cleavage of Alzheimer's amyloid precursor protein by the transmembrane aspartic protease BACE," *Science*, 286:735-741, 1999.
Yan et al., "Membrane-anchored aspartyl protease with Alzheimer's disease beta-secretase activity," *Nature*, 402:533-537, 1999.
Zhao et al., "β-site amyloid precursor protein cleaving enzyme I levels become elevated in neurons around amyloid plaques: implications for Alzheimer's disease pathogenesis," *J. Neurosci.*, 27:3639-49, 2007.

* cited by examiner

*Primary Examiner* — Olga N Chernyshev
(74) *Attorney, Agent, or Firm* — Fulbright & Jaworski

(57) ABSTRACT

This application pertains to antibodies which specifically bind to immunogenic memapsin 2β-secretase peptides for use in the treatment of Alzheimer's disease and memapsin 2β-secretase disorders. The application also pertains to immunogenic compositions comprising memapsin 2β-secretase peptides and uses thereof.

9 Claims, 14 Drawing Sheets

MASMTGGQQMGRGSMAGVLPAHGTQHGIRLPLRSGLGGAPLGLRLPRETDEEPEEPGRRGSFVEMVDNLRGKSGQGYYVE

MTVGSPPPQTLNILVDTGSSNFAVGAAPHPFLHRYYQRQLSSTYRDLRKGVYYPYTQGKWEGELGTDLVSIPHGPNVTVRA

NIAAITESDKFFINGSNWEGILGLAYAEIARPDDSLEPFFDSLVKQTHVPNLFSLQLCGAGFPLNQSEVLASVGGSMIIG

GIDHSLYTGSLWYTPIRREWYYEVIIVRVEINGQDLKMDCKEYNYDKSIVDSGTTNLRLPKKVFEAAVKSIKAASSTEKF

PDGFWLGEQLVCWQAGTTPWNIFPVISLYLMGEVTNQSFRITILPQQYLRPVEDVATSQDDCYKFAISQSSTGTVMGAVI

MEGFYVVFDRARKRIGFAVSACHVHDEFRTAAVEGPFVTLDMEDCGYNIPQTDEST

FIG. 1

```
Pin
Number   Decapeptide Amino Acid Sequence
   1     LRLPRETDEE
   2         LPRETDEEPE
   3             RETDEEPEEP
   4                 TDEEPEEPGR
   5                     EEPEEPGRRG
   6                         PEEPGRRGSF
   7                             EPGRRGSFVE
   8                                 GRRGSFVEMV
   9                                     RGSFVEMVD
   .                                     .........
   .                                     .........
   .                                     .........
   .
  201                                                 EDCGYNIPQT
  202                                                     CGYNIPQTDE
  203                                                         YNIPQTDEST Memapsin 2 Sequence
         1
393
           .
.
LRLPRETDEEPEEPGRRGSFVEMVD............................EDCGYNIPQTDEST
           .
.
          43
456
```

FIG. 2

```
        -60       -50       -40       -30       -20       -10        1        10
MASMTGGQQMGRGSMAGVLPAHGTQHGIRLPLRSGLGGAPLGLRLPRETDEEPEEPGRGSFVEMVDNLRGKSGQGYYVE
                                                   Region 5 (-15 to 13)

20        30        40        50        60        70        80        90
MTVGSPPQTLNILVDTGSSNFAVGAAPHPFLHRYYQRQLSSTYRDLRKGVYVPYTQGKWEGELGTDLVSIPHGPNVTVRA
                                             Region 2 (64 to 99)

100       110       120       130       140       150       160       170
NIAAITESDKFFINGSNWEGILGLAYAEIARPDDSLEPFFDSLVKQTHVPNLFSLQLCGAGFPLNQSEVLASVGGSMIIG
                         Region 3 (120 to 169)

180       190       200       210       220       230       240       250
GIDHSLYTGSLWYTPIRREWYYEVIIVRVEINGQDLKMDCKEYNYDKSIVDSGTTNLRLPKKVFEAAVKSIKAASSTEKF
                                           Region 1 (214 to 251)

260       270       280       290       300       310       320       330
PDGFWLGEQLVCWQAGTTPWNIFPVISLYLMGEVTNQSFRITILPQQYLRPVEDVATSQDDCYKFAISQSSTGTVMGAVI
                            Region 6 (288 to 321)

340       350       360       370       380       390
MEGFYVVFDRARKRIGFAVSACHVHDEFRTAAVEGPFVTLDMEDCGYNIPQTDEST
                              Region 4 (370 to 393)
```

FIG. 4

| Name | Human Memapsin 2 Peptide Sequence | Octapeptide PIN# |
|---|---|---|
| #1-a (26-mer) | KMDCKEYNYDKSIVDSGTTNLRLPKK<br>214                                                   239 | 118-126 |
| #1-b (18-mer) | LRLPKKVFEAAVKSIKAA<br>234              251 | 128-132 |
| #2 (36-mer) | RKGVYVPYTQGKWEGELGTDLVSIPHGPNVTVRANI<br>64                                                                    99 | 43-56 |

FIG. 5

| Name | Amino Acid Sequence |
|---|---|
| Peptide 1a | KMDCKEYNYDKSIVDSGTTNLRLPKK |
| Peptide 2a | RKGVYVPYTQGKWEGE |

FIG. 6

```
1000L  DVLMTQTPLSLPVSLGDQASISCRSSQSLVHSNGN-TYLHWYLQKPGQSPKLLIYKVSNR
1001L  DIVLTQSPASLAVSLGQRATISYRASKSVSTSGY--SYMHWNQQKPGQPPRLLIYLVSNL
1002L  DVLMTQTPLTLSVTIGQPASISCKSSQSLLDSGGR-TYLNWLLQRPGQSPKRLIYLVSKL
1003L  DIQMTQSPSSLAVSAGEKVTMSCKSSQSLLNSRTRKNYLAWYQQKPGQSPKLLIYWASTR
1004L  DVLMTQTPLTLSVTIGHPASISCKSSQSLLDSNGR-TYLNWLLQRPGQSPKRLIYLVSKV
2000L  --VLTQSPGSLAVSLGQRATISCRASESVEYYGT--SLMQWYQQRPGQPPKLLIYAASNV
2001L  DVLMTQTPLSLPVSLGDQASISCRSSQSTVHSNGN-TYLEWYLQKPGQSPKLLIYK-SNR
2002L  DIQMTQSPSSLAVSAGEKVTMSCKSSQSLLNSRTRKNYLAWYQQKPGQSPKLLIYWASTR
2003L  ---LTQSPALMSASPGEKVTMTCSASSSV------SHMYWYQQKPRSSPKPWIHLTSNR

1000L  FSGVPDRFSGSGSGTDFTLKISRVEAEDLGVYFCSQTTHIPWTFGGGTKL----
1001L  ESGVPARLSGSGSGTDFTLNIHPVEEEDAATYYCQHIRELTRSEGAPSWKSN--
1002L  DSGVPDRFTGSGSGTDFTLKISRVEAEDLGVYYCWQGTHSPHTFGGGTKLEIKR
1003L  ESGVPDRFTGSGSGTDFTLTISSVQAEDLAVYYC-KQSYILPTFGGGTKLEIKR
1004L  DSGVPDRFTGSGSGTDFTLKISRVEAEDLGVYYCWQGTHYPYTFGGGTKLEIKR
2000L  ESGVPARFSGSGSGTDFSLNIQPVEEDDIAMYFCQQSRKIPWTFGGGTKLEIK-
2001L  FSGVPDRFSGSGSGTDFTLKISRVEAEDLGVYYCFQGSHVPPTFGGGTKLEIKR
2002L  ESGVPDRFTGSGSGTDFTLTISSVQAEDLAVYYC-KQSYNLWTFGGGTKLEIKR
2003L  ASGVPARFSGSGSGTSYSLTISSMEAEDTATYYCQQWSGNPLTFGAGTKLELKR
```

FIG. 12A

```
1000H  VQLQQSGAELAKPGASVKMSCKASGYTFTNY-WMHWVKQRPGQGLEWIGYINPTTGYTEY
1001H  VKLQESGAELVKPGASVKLSCKASGYTFSSY-WIHWVKQRAGQGLEWIGNIKPKSGRTNY
1002H  VKLQESGPGLVRPSQSLSVTCNVIGYSITSGYYWNWIRQFPGNKLEWMDYIH-NTNSTSY
1003H  -----SGAELVRPGASVKMSCKASGYTFTTY-TMHWVKQTPGQGLEWIGAIYPGNGGTSY
1004H  VKLQESGPGLVKPSQSLSVTCTVTGYSITTDY*WNWNRQFSGNQLEWMGYIY-NSGSTNY
2000H  VQLQESGGGLVQPGRSRKLSCATSGFTFSRY-GMHWVRQAPEKGLEWVAYINSSSGNIYY
2002H  ------------------SCKASGYTFTDY-NMHWVKQNQGKSLEWIGEINPNNGGTDY
2003H  -----SGPEMVKPGASVKISCKASGYTFTDY-SMHWVKQSHGKSLEWIGRVNPNNGGTRF

1000H  NQKFKDKATLTADKSSSTAYMQLNSLTSEDSAVYYCVRSDY--TRGYWG-------QGTTVTVSS
1001H  NAKFKNKATLTEDTSSSTVYIQLSSLTFEDSAVYYCTRD------DYWG-------QGTTVTVSS
1002H  NPSLKSRLSVTRDTSKNHFFLQLNSVTTEDTATHYCARSGA--NYYYPTMLWTTGAKGPRSPSPQ
1003H  NQKFKGMATLTVDTSSSTAYMQISSLTSEDSAVYFCARGGDKYGMDYWG-------QGTTVTVSS
1004H  NPSLKSRISITRDTSKNQFFLLMCKIGGLL**PYYAMDYWGQGTTVTVS---------------
2000H  ADTVKGRFTISRDNAKNTLFLQMTSLRSEDTAMYYCARQGY--DVYYA-VDYWG-QGTTVTVSS
2002H  TQKFKGKATLTVDKSSSTAYMELRSLTSEDSAVYYCVRT------RYWG-------QGTTVTVSS
2003H  NQKFEGKATLTVDKSSSTAYMELNSLTSDDSAVYYCAISAR--ALDIWG-------QGTTVTVSS
```

FIG. 12B

| Name | Isotype | Epitope | Titer[#] (against hM2$_{ED}$) |
|---|---|---|---|
| M2 1000 | IgG2a$_\kappa$ | Pep-1 | $4.1 \times 10^5$ |
| M2 1001 | IgG1$_\kappa$ | Pep-1 | $3.0 \times 10^5$ |
| M2 1002 | IgG2b$_\kappa$ | Pep-1 | $1.5 \times 10^5$ |
| M2 1003 | IgG1$_\kappa$ | Pep-2 | $5.9 \times 10^5$ |
| M2 1004 | IgG1$_\kappa$ | Pep-1 | $4.5 \times 10^5$ |
| M2 2000 | IgG1$_\kappa$ | n.a. | $6.9 \times 10^5$ |
| M2 2001 | IgG2b$_\kappa$ | n.a. | $3.1 \times 10^5$ |
| M2 2002 | IgG1$_\kappa$ | n.a. | n.a. |
| M2 2003 | IgG1$_\kappa$ | n.a. | n.a. |

[#] Antibody titer under a fixed concentration (20 mg/ml)

n.a. not available

FIG. 13

SEQUENCE LISTING

<160> NUMBER OF SEQ ID NOS: 36

<210> SEQ ID NO 1
<211> LENGTH: 26
<212> TYPE: PRT
<213> ORGANISM: Homo sapiens

<400> SEQUENCE: 1

Lys Met Asp Cys Lys Glu Tyr Asn Tyr Asp Lys Ser Ile Val Asp Ser
1               5                   10                  15

Gly Thr Thr Asn Leu Arg Leu Pro Lys Lys
            20                  25

```
<210> SEQ ID NO 2
<211> LENGTH: 18
<212> TYPE: PRT
<213> ORGANISM: Homo sapiens

<400> SEQUENCE: 2

Leu Arg Leu Pro Lys Lys Val Phe Glu Ala Ala Val Lys Ser Ile Lys
1               5                   10                  15

Ala Ala

<210> SEQ ID NO 3
<211> LENGTH: 36
<212> TYPE: PRT
<213> ORGANISM: Homo sapiens

<400> SEQUENCE: 3

Arg Lys Gly Val Tyr Val Pro Tyr Thr Gln Gly Lys Trp Glu Gly Glu
1               5                   10                  15

Leu Gly Thr Asp Leu Val Ser Ile Pro His Gly Pro Asn Val Thr Val
                20                  25                  30

Arg Ala Asn Ile
            35

<210> SEQ ID NO 4
<211> LENGTH: 50
<212> TYPE: PRT
<213> ORGANISM: Homo sapiens

<400> SEQUENCE: 4

Gly Leu Ala Tyr Ala Glu Ile Ala Arg Pro Asp Asp Ser Leu Glu Pro
1               5                   10                  15

Phe Phe Asp Ser Leu Val Lys Gln Thr His Val Pro Asn Leu Phe Ser
                20                  25                  30

Leu Gln Leu Cys Gly Ala Gly Phe Pro Leu Asn Gln Ser Glu Val Leu
                35                  40                  45

Ala Ser
    50

<210> SEQ ID NO 5
<211> LENGTH: 24
<212> TYPE: PRT
<213> ORGANISM: Homo sapiens

<400> SEQUENCE: 5

Val Glu Gly Pro Phe Val Thr Leu Asp Met Glu Asp Cys Gly Tyr Asn
1               5                   10                  15

Ile Pro Gln Thr Asp Glu Ser Thr
                20

<210> SEQ ID NO 6
<211> LENGTH: 28
<212> TYPE: PRT
<213> ORGANISM: Homo sapiens

<400> SEQUENCE: 6

Thr Asp Glu Glu Pro Glu Glu Pro Gly Arg Arg Gly Ser Phe Val Glu
1               5                   10                  15

Met Val Asp Asn Leu Arg Gly Lys Ser Gly Gln Gly
                20                  25
```

<210> SEQ ID NO 7
<211> LENGTH: 34
<212> TYPE: PRT
<213> ORGANISM: Homo sapiens

<400> SEQUENCE: 7

```
Met Gly Glu Val Thr Asn Gln Ser Arg Phe Ile Thr Ile Leu Pro Gln
 1               5                  10                  15

Gln Tyr Leu Arg Pro Val Glu Asp Val Ala Thr Ser Gln Asp Asp Cys
            20                  25                  30

Tyr Lys
```

<210> SEQ ID NO 8
<211> LENGTH: 456
<212> TYPE: PRT
<213> ORGANISM: Homo sapiens

<400> SEQUENCE: 8

```
Met Ala Ser Met Thr Gly Gly Gln Gln Met Gly Arg Gly Ser Met Ala
 1               5                  10                  15

Gly Val Leu Pro Ala His Gly Thr Gln His Gly Ile Arg Leu Pro Leu
            20                  25                  30

Arg Ser Gly Leu Gly Gly Ala Pro Leu Gly Leu Arg Leu Pro Arg Glu
        35                  40                  45

Thr Asp Glu Glu Pro Glu Glu Pro Gly Arg Arg Gly Ser Phe Val Glu
 50                  55                  60

Met Val Asp Asn Leu Arg Gly Lys Ser Gly Gln Gly Tyr Tyr Val Glu
 65                  70                  75                  80

Met Thr Val Gly Ser Pro Pro Gln Thr Leu Asn Ile Leu Val Asp Thr
                85                  90                  95

Gly Ser Ser Asn Phe Ala Val Gly Ala Ala Pro His Pro Phe Leu His
            100                 105                 110

Arg Tyr Tyr Gln Arg Gln Leu Ser Ser Thr Tyr Arg Asp Leu Arg Lys
        115                 120                 125

Gly Val Tyr Val Pro Tyr Thr Gln Gly Lys Trp Glu Gly Glu Leu Gly
    130                 135                 140

Thr Asp Leu Val Ser Ile Pro His Gly Pro Asn Val Thr Val Arg Ala
145                 150                 155                 160

Asn Ile Ala Ala Ile Thr Glu Ser Asp Lys Phe Phe Ile Asn Gly Ser
                165                 170                 175

Asn Trp Glu Gly Ile Leu Gly Leu Ala Tyr Ala Glu Ile Ala Arg Pro
            180                 185                 190

Asp Asp Ser Leu Glu Pro Phe Phe Asp Ser Leu Val Lys Gln Thr His
        195                 200                 205

Val Pro Asn Leu Phe Ser Leu Gln Leu Cys Gly Ala Gly Phe Pro Leu
    210                 215                 220

Asn Gln Ser Glu Val Leu Ala Ser Val Gly Gly Ser Met Ile Ile Gly
225                 230                 235                 240

Gly Ile Asp His Ser Leu Tyr Thr Gly Ser Leu Trp Tyr Thr Pro Ile
                245                 250                 255

Arg Arg Glu Trp Tyr Tyr Glu Val Ile Ile Val Arg Val Glu Ile Asn
            260                 265                 270

Gly Gln Asp Leu Lys Met Asp Cys Lys Glu Tyr Asn Tyr Asp Lys Ser
        275                 280                 285

Ile Val Asp Ser Gly Thr Thr Asn Leu Arg Leu Pro Lys Lys Val Phe
    290                 295                 300
```

```
Glu Ala Ala Val Lys Ser Ile Lys Ala Ser Ser Thr Glu Lys Phe
305                 310                 315                 320

Pro Asp Gly Phe Trp Leu Gly Glu Gln Leu Val Cys Trp Gln Ala Gly
            325                 330                 335

Thr Thr Pro Trp Asn Ile Phe Pro Val Ile Ser Leu Tyr Leu Met Gly
        340                 345                 350

Glu Val Thr Asn Gln Ser Phe Arg Ile Thr Ile Leu Pro Gln Gln Tyr
    355                 360                 365

Leu Arg Pro Val Glu Asp Val Ala Thr Ser Gln Asp Asp Cys Tyr Lys
370                 375                 380

Phe Ala Ile Ser Gln Ser Ser Thr Gly Thr Val Met Gly Ala Val Ile
385                 390                 395                 400

Met Glu Gly Phe Tyr Val Val Phe Asp Arg Ala Arg Lys Arg Ile Gly
            405                 410                 415

Phe Ala Val Ser Ala Cys His Val His Asp Glu Phe Arg Thr Ala Ala
            420                 425                 430

Val Glu Gly Pro Phe Val Thr Leu Asp Met Glu Asp Cys Gly Tyr Asn
        435                 440                 445

Ile Pro Gln Thr Asp Glu Ser Thr
    450                 455

<210> SEQ ID NO 9
<211> LENGTH: 109
<212> TYPE: PRT
<213> ORGANISM: Homo sapiens

<400> SEQUENCE: 9

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Ile Pro Trp Thr Phe Gly Gly Gly Thr Lys Leu
            100                 105

<210> SEQ ID NO 10
<211> LENGTH: 340
<212> TYPE: DNA
<213> ORGANISM: Homo sapiens

<400> SEQUENCE: 10
ccgtttgatt tacagcttgg tgcctccacc gaacgtccac ggaatatgtg tagtttgaga      60
gcagaaataa actcccagat cctcagcctc cactctgctg atcttgagtg tgaaatctgt     120
ccctgatcca ctgccactga acctgtctgg gaccccagaa aatcgattgg aaactttgta     180
gatcaggagt tttggagact ggcctggctt ctgcaggtac caatgtaaat aggtgtttcc     240
attactgtgt acaaggctct gactagatct gcaagagatg gaggcttgat ctccaagact     300
gacaggcagg gagagtggag tttgggtcat caaaacatca                           340
```

```
<210> SEQ ID NO 11
<211> LENGTH: 116
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 11

Xaa Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Asn Tyr
            20                  25                  30

Trp Met His Val Lys Gln Arg Pro Gly Gln Gly Leu Glu Trp Ile
        35                  40                  45

Gly Tyr Ile Asn Pro Thr Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Val Arg Ser Asp Tyr Thr Arg Gly Tyr Trp Gly Gln Gly Thr Thr Val
            100                 105                 110

Thr Val Ser Ser
        115

<210> SEQ ID NO 12
<211> LENGTH: 348
<212> TYPE: DNA
<213> ORGANISM: Homo sapiens
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t

<400> SEQUENCE: 12
aggtgaagct gcaggagtcn ggggctgaag tggcaaaacc tggggcctct ctgaagatgt      60
cctgcaaggc ttcgggctac tcctttacta actactggat gcactgggna aaacagatgc    120
ctggacaggg tctggagngg attggataca ttaatcctac cgctggttat actgagtacc    180
atcanaagtt canggacaag gccacattga ctgcagacaa atcctccagc agaccctaca    240
tgcaattgaa cagcctgact tctgatgact ctgctgtcta ttattgtgta agatctgact    300
ataccagagg gtactggggg caacggacca cggtcaccgt ctcctcaa                 348

<210> SEQ ID NO 13
<211> LENGTH: 113
<212> TYPE: PRT
<213> ORGANISM: Homo sapiens
```

<400> SEQUENCE: 13

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Gly Gly Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro His Thr Phe Gly Gly Gly Thr Lys Leu Glu Ile Lys
            100                 105                 110

Arg

<210> SEQ ID NO 14
<211> LENGTH: 340
<212> TYPE: DNA
<213> ORGANISM: Homo sapiens

<400> SEQUENCE: 14
gatgttttga tgacccaaac tccactcact ttgtcggtta ccattggaca accagcctcc      60
atctcttgca agtcaagtca gagcctctta gatagtggtg aaggacata tttgaattgg     120 ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattctcct     300
cacacgttcg gagggggcac caagctggaa atcaaacgga                          340

<210> SEQ ID NO 15
<211> LENGTH: 122
<212> TYPE: PRT
<213> ORGANISM: Homo sapiens

<400> SEQUENCE: 15

Val Lys Leu Gln Glu Ser Gly Pro Gly Leu Val Arg Pro Ser Gln Ser
1               5                   10                  15

Leu Ser Val Thr Cys Asn Val Ile Gly Tyr Ser Ile Thr Ser Gly Tyr
            20                  25                  30

Tyr Trp Asn Trp Ile Arg Gln Phe Pro Gly Asn Lys Leu Glu Trp Met
        35                  40                  45

Asp Tyr Ile His Asn Thr Asn Ser Thr Ser Tyr Asn Pro Ser Leu Lys
    50                  55                  60

Ser Arg Leu Ser Val Thr Arg Asp Thr Ser Lys Asn His Phe Phe Leu
65                  70                  75                  80

Gln Leu Asn Ser Val Thr Thr Glu Asp Thr Ala Thr His Tyr Cys Ala
                85                  90                  95

Arg Ser Gly Ala Asn Tyr Tyr Tyr Pro Thr Met Leu Trp Thr Thr Gly
            100                 105                 110

Ala Lys Gly Pro Arg Ser Pro Ser Pro Gln
        115                 120

```
<210> SEQ ID NO 16
<211> LENGTH: 368
<212> TYPE: DNA
<213> ORGANISM: Homo sapiens

<400> SEQUENCE: 16
aggtgaaact gcaggagtct ggacctggcc tggtgagacc ttctcagtct ctgtccgtca      60
cctgcaatgt cattggctac tccatcacca gtggttatta ctggaactgg atccggcagt     120
ttccgggaaa caaactggag tggatggact acatacacaa tactaatagc actagctaca     180
acccatctct caaaagtcga ctctctgtca ctcgagacac atccaagaac cacttcttcc     240
tgcagttgaa ttctgtgact acggaggaca cagccacaca ttactgtgca agatcggggg     300
ccaactatta ttaccctact atgctatgga ctactggggc aagggaccac ggtcaccgt      360
ctcctcaa                                                               368

<210> SEQ ID NO 17
<211> LENGTH: 113
<212> TYPE: PRT
<213> ORGANISM: Homo sapiens

<400> SEQUENCE: 17

Asp Ile Gln Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Ile Leu Pro Thr Phe Gly Gly Gly Thr Lys Leu Glu Ile Lys
            100                 105                 110

Arg

<210> SEQ ID NO 18
<211> LENGTH: 339
<212> TYPE: DNA
<213> ORGANISM: Homo sapiens

<400> SEQUENCE: 18
gacatccaga tgacccagtc tccatcctcc ctggctgtgt cagcaggaga gaaggtcact      60
atgagctgca aatccagtca gagtctgctc aacagtagaa cccgaaagaa ctacttggct     120
tggtatcagc agaaaccagg gcagtctcct aaactgctga tctactgggc atccactagg     180
gaatctgggg tccctgatcg cttcacaggc agtggatctg gacagattt cactctcacc      240
atcagcagtg tgcaggctga agacctgca gtttattact gtaagcaatc ttatattctt      300
ccgacgttcg gtggagggac caagctggaa ataaaacga                            339

<210> SEQ ID NO 19
<211> LENGTH: 112
<212> TYPE: PRT
<213> ORGANISM: Homo sapiens
```

```
<400> SEQUENCE: 19

Ser Gly Ala Glu Leu Val Arg Pro Gly Ala Ser Val Lys Met Ser Cys
1               5                   10                  15

Lys Ala Ser Gly Tyr Thr Phe Thr Thr Tyr Thr Met His Trp Val Lys
            20                  25                  30

Gln Thr Pro Gly Gln Gly Leu Glu Trp Ile Gly Ala Ile Tyr Pro Gly
        35                  40                  45

Asn Gly Gly Thr Ser Tyr Asn Gln Lys Phe Lys Gly Met Ala Thr Leu
    50                  55                  60

Thr Val Asp Thr Ser Ser Thr Ala Tyr Met Gln Ile Ser Ser Leu
65                  70                  75                  80

Thr Ser Glu Asp Ser Ala Val Tyr Phe Cys Ala Arg Gly Gly Asp Lys
                85                  90                  95

Tyr Gly Met Asp Tyr Trp Gly Gln Gly Thr Thr Val Thr Val Ser Ser
            100                 105                 110

<210> SEQ ID NO 20
<211> LENGTH: 354
<212> TYPE: DNA
<213> ORGANISM: Homo sapiens

<400> SEQUENCE: 20
aggtgcagct gcagcagtct ggggctgagc tggtgaggcc tggggcctca gtgaagatgt    60
cctgcaaggc ttctggctac acatttacca cttacactat gcactgggta aagcagaccc   120
ctggacaggg cctggaatgg attggagcta tttatccagg aaatggtggt acttcctaca   180
atcagaagtt caaggcatg gccacactga ctgtagacac atcctccagc acagcgtaca   240
tgcagatcag cagcctgaca tctgaagact ctgcggtcta tttctgtgca agagggggg   300 ataaatatgg tatggactac tggggccaag ggaccacggt caccgtctcc tcaa          354

<210> SEQ ID NO 21
<211> LENGTH: 109
<212> TYPE: PRT
<213> ORGANISM: Homo sapiens

<400> SEQUENCE: 21

Val Leu Thr Gln Ser Pro Gly Ser Leu Ala Val Ser Leu Gly Gln Arg
1               5                   10                  15

Ala Thr Ile Ser Cys Arg Ala Ser Glu Ser Val Glu Tyr Tyr Gly Thr
            20                  25                  30

Ser Leu Met Gln Trp Tyr Gln Gln Arg Pro Gly Gln Pro Pro Lys Leu
        35                  40                  45

Leu Ile Tyr Ala Ala Ser Asn Val Glu Ser Gly Val Pro Ala Arg Phe
    50                  55                  60

Ser Gly Ser Gly Ser Gly Thr Asp Phe Ser Leu Asn Ile Gln Pro Val
65                  70                  75                  80

Glu Glu Asp Asp Ile Ala Met Tyr Phe Cys Gln Gln Ser Arg Lys Ile
                85                  90                  95

Pro Trp Thr Phe Gly Gly Gly Thr Lys Leu Glu Ile Lys
            100                 105

<210> SEQ ID NO 22
<211> LENGTH: 335
<212> TYPE: DNA
<213> ORGANISM: Homo sapiens
```

<400> SEQUENCE: 22

```
gaaaatgtgc tcacccagtc tccaggttct ttggctgtgt ctctagggca gagagccacc      60
atctcctgca gagccagtga aagtgttgaa tattatggca caagtttaat gcagtggtac     120
caacagagac caggacagcc acccaaactc ctcatctatg ctgcatccaa cgttgaatct     180
ggggtccctg ccaggtttag tggcagtgga tctgggacag acttcagcct caacatccaa     240
cctgtggagg aggatgatat tgcaatgtat ttctgtcagc aaagtaggaa gattccgtgg     300
acgttcggtg gaggcaccaa gctggaaatc aaaca                                335
```

<210> SEQ ID NO 23
<211> LENGTH: 120
<212> TYPE: PRT
<213> ORGANISM: Homo sapiens

<400> SEQUENCE: 23

```
Val Gln Leu Gln Glu Ser Gly Gly Leu Val Gln Pro Gly Arg Ser
1               5                   10                  15
Arg Lys Leu Ser Cys Ala Thr Ser Gly Phe Thr Phe Ser Arg Tyr Gly
            20                  25                  30
Met His Trp Val Arg Gln Ala Pro Glu Lys Gly Leu Glu Trp Val Ala
        35                  40                  45
Tyr Ile Asn Ser Ser Gly Asn Ile Tyr Tyr Ala Asp Thr Val Lys
    50                  55                  60
Gly Arg Phe Thr Ile Ser Arg Asp Asn Ala Lys Asn Thr Leu Phe Leu
65                  70                  75                  80
Gln Met Thr Ser Leu Arg Ser Glu Asp Thr Ala Met Tyr Tyr Cys Ala
                85                  90                  95
Arg Gln Gly Tyr Asp Val Tyr Tyr Ala Val Asp Tyr Trp Gly Gln
            100                 105                 110
Gly Thr Thr Val Thr Val Ser Ser
        115                 120
```

<210> SEQ ID NO 24
<211> LENGTH: 363
<212> TYPE: DNA
<213> ORGANISM: Homo sapiens

<400> SEQUENCE: 24

```
tgaggagacg gtgaccgtgg tcccttggcc ccagtagtcc acagcatagt aatatacgtc      60
gtaaccctgt cttgcacagt aatacatggc cgtgtcctca gaccttagac tggtcatttg     120
caggaacagg gtgttcttgg cattgtctct ggagatggtg aatcggccct tcactgtgtc     180
tgcatagtag atgttaccac tactactatt aatatatgcg acccactcca gccccttctc     240
tggagcctga cgaacccagt gcattccata gcgactgaaa gtgaatccag aggttgcaca     300
ggagagtttc cgggaccgtc caggctgcac taagcctccc ccagactcct gcagctgcac     360
cta                                                                   363
```

<210> SEQ ID NO 25
<211> LENGTH: 112
<212> TYPE: PRT
<213> ORGANISM: Homo sapiens

<400> SEQUENCE: 25

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Thr Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Ser Asn Arg Phe Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Leu Gly Val Tyr Tyr Cys Phe Gln Gly Ser
                85                  90                  95

His Val Pro Pro Thr Phe Gly Gly Gly Thr Lys Leu Glu Ile Lys Arg
            100                 105                 110

<210> SEQ ID NO 26
<211> LENGTH: 340
<212> TYPE: DNA
<213> ORGANISM: Homo sapiens

<400> SEQUENCE: 26
gatgttttga tgacccaaac tccactctcc ctgcctgtca gtcttggaga tcaagcctcc      60
atctcttgca gatctagtca gagcactgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
ccgacgttcg gtggaggcac caagctggaa atcaaacgga                           340

<210> SEQ ID NO 27
<211> LENGTH: 104
<212> TYPE: PRT
<213> ORGANISM: Homo sapiens

<400> SEQUENCE: 27

Leu Thr Gln Ser Pro Ala Leu Met Ser Ala Ser Pro Gly Glu Lys Val
1               5                   10                  15

Thr Met Thr Cys Ser Ala Ser Ser Val Ser His Met Tyr Trp Tyr
            20                  25                  30

Gln Gln Lys Pro Arg Ser Ser Pro Lys Pro Trp Ile His Leu Thr Ser
        35                  40                  45

Asn Arg Ala Ser Gly Val Pro Ala Arg Phe Ser Gly Ser Gly Ser Gly
    50                  55                  60

Thr Ser Tyr Ser Leu Thr Ile Ser Ser Met Glu Ala Glu Asp Thr Ala
65                  70                  75                  80

Thr Tyr Tyr Cys Gln Gln Trp Ser Gly Asn Pro Leu Thr Phe Gly Ala
                85                  90                  95

Gly Thr Lys Leu Glu Leu Lys Arg
            100

<210> SEQ ID NO 28
<211> LENGTH: 322
<212> TYPE: DNA
<213> ORGANISM: Homo sapiens -continued

```
<400> SEQUENCE: 28
gaaaatgtgc tcacccagtc tccagcactc atgtctgcat ctccagggga gaaggtcacc    60
atgacctgca gtgccagctc aagtgtaagt cacatgtact ggtaccagca gaagccaaga   120
tcctccccca aaccctggat tcatctcaca tccaaccggg cttctggagt ccctgctcgc   180
ttcagtggca gtgggtctgg gacctcttac tctctcacaa tcagcagcat ggaggctgaa   240
gatactgcca cttattactg ccagcagtgg agtggtaacc cgctcacgtt cggtgctggg   300
accaagctgg agctgaaacg ga                                            322

<210> SEQ ID NO 29
<211> LENGTH: 110
<212> TYPE: PRT
<213> ORGANISM: Homo sapiens

<400> SEQUENCE: 29

Ser Gly Pro Glu Met Val Lys Pro Gly Ala Ser Val Lys Ile Ser Cys
 1               5                  10                  15

Lys Ala Ser Gly Tyr Thr Phe Thr Asp Tyr Ser Met His Trp Val Lys
            20                  25                  30

Gln Ser His Gly Lys Ser Leu Glu Trp Ile Gly Arg Val Asn Pro Asn
        35                  40                  45

Asn Gly Gly Thr Arg Phe Asn Gln Lys Phe Glu Gly Lys Ala Thr Leu
    50                  55                  60

Thr Val Asp Lys Ser Ser Ser Thr Ala Tyr Met Glu Leu Asn Ser Leu
65                  70                  75                  80

Thr Ser Asp Asp Ser Ala Val Tyr Tyr Cys Ala Ile Ser Ala Arg Ala
                85                  90                  95

Leu Asp Ile Trp Gly Gln Gly Thr Thr Val Thr Val Ser Ser
            100                 105                 110

<210> SEQ ID NO 30
<211> LENGTH: 348
<212> TYPE: DNA
<213> ORGANISM: Homo sapiens

<400> SEQUENCE: 30
aggtcaaact gcaggagtca ggacctgaga tggtgaagcc tggggcttca gtgaagatat    60
cctgcaaggc ttctggatac acattcactg actactccat gcactgggtg aagcagagcc   120
atggaaagag ccttgagtgg attggacgtg ttaatcctaa caatggtggt actaggttca   180
accagaagtt cgagggcaag gccacattga ctgttgacaa atcctccagc acagcctaca   240
tggaactcaa cagcctaaca tctgatgact ctgcggtcta ttactgtgca atatcggctc   300
gggctcttga catctggggc caagggacca cggtcaccgt ctcctcaa                348

<210> SEQ ID NO 31
<211> LENGTH: 110
<212> TYPE: PRT
<213> ORGANISM: Homo sapiens

<400> SEQUENCE: 31

Asp Ile Val Leu Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45
```

Arg Leu Leu Ile Tyr Leu Val Ser Asn Leu Glu Ser Gly Val Pro Ala
 50                  55                  60

Arg Leu Ser Gly Ser Gly Ser Gly Thr Asp Phe Thr Leu Asn Ile His
65                  70                  75                  80

Pro Val Glu Glu Asp Ala Ala Thr Tyr Tyr Cys Gln His Ile Arg
                85                  90                  95

Glu Leu Thr Arg Ser Glu Gly Ala Pro Ser Trp Lys Ser Asn
            100                 105                 110

<210> SEQ ID NO 32
<211> LENGTH: 111
<212> TYPE: PRT
<213> ORGANISM: Homo sapiens

<400> SEQUENCE: 32

Val Lys Leu Gln Glu Ser Gly Ala Glu Leu Val Lys Pro Gly Ala Ser
1               5                   10                  15

Val Lys Leu Ser Cys Lys Ala Ser Gly Tyr Thr Phe Ser Ser Tyr Trp
            20                  25                  30

Ile His Trp Val Lys Gln Arg Ala Gly Gln Gly Leu Glu Trp Ile Gly
        35                  40                  45

Asn Ile Lys Pro Lys Ser Gly Arg Thr Asn Tyr Asn Ala Lys Phe Lys
 50                 55                  60

Asn Lys Ala Thr Leu Thr Glu Asp Thr Ser Ser Ser Thr Val Tyr Ile
65                  70                  75                  80

Gln Leu Ser Ser Leu Thr Phe Glu Asp Ser Ala Val Tyr Tyr Cys Thr
                85                  90                  95

Arg Asp Asp Tyr Trp Gly Gln Gly Thr Thr Val Thr Val Ser Ser
            100                 105                 110

<210> SEQ ID NO 33
<211> LENGTH: 113
<212> TYPE: PRT
<213> ORGANISM: Homo sapiens

<400> SEQUENCE: 33

Asp Val Leu Met Thr Gln Thr Pro Leu Thr Leu Ser Val Thr Ile Gly
1               5                   10                  15

His Pro Ala Ser Ile Ser Cys Lys Ser Ser Gln Ser Leu Leu Asp Ser
            20                  25                  30

Asn Gly Arg Thr Tyr Leu Asn Trp Leu Leu Gln Arg Pro Gly Gln Ser
        35                  40                  45

Pro Lys Arg Leu Ile Tyr Leu Val Ser Lys Val Asp Ser Gly Val Pro
 50                 55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Tyr Pro Tyr Thr Phe Gly Gly Gly Thr Lys Leu Glu Ile Lys
            100                 105                 110

Arg

<210> SEQ ID NO 34
<211> LENGTH: 105
<212> TYPE: PRT
<213> ORGANISM: Homo sapiens

```
<400> SEQUENCE: 34

Val Lys Leu Gln Glu Ser Gly Pro Gly Leu Val Lys Pro Ser Gln Ser
1               5                   10                  15

Leu Ser Val Thr Cys Thr Val Thr Gly Tyr Ser Ile Thr Thr Asp Tyr
            20                  25                  30

Trp Asn Trp Asn Arg Gln Phe Ser Gly Asn Gln Leu Glu Trp Met Gly
            35                  40                  45

Tyr Ile Tyr Asn Ser Gly Ser Thr Asn Tyr Asn Pro Ser Leu Lys Ser
        50                  55                  60

Arg Ile Ser Ile Thr Arg Asp Thr Ser Lys Asn Gln Phe Phe Leu Leu
65                  70                  75                  80

Met Cys Lys Ile Gly Gly Leu Leu Pro Tyr Tyr Ala Met Asp Tyr Trp
                85                  90                  95

Gly Gln Gly Thr Thr Val Thr Val Ser
            100                 105

<210> SEQ ID NO 35
<211> LENGTH: 113
<212> TYPE: PRT
<213> ORGANISM: Homo sapiens

<400> SEQUENCE: 35

Asp Ile Gln Met Thr Gln Ser Pro Ser Ser Leu Ala Val Ser Ala Gly
1               5                   10                  15

Glu Lys Val Thr Met Ser Cys Lys Ser Gln Ser Leu Leu Asn Ser
            20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

Arg

<210> SEQ ID NO 36
<211> LENGTH: 92
<212> TYPE: PRT
<213> ORGANISM: Homo sapiens

<400> SEQUENCE: 36

Ser Cys Lys Ala Ser Gly Tyr Thr Phe Thr Asp Tyr Asn Met His Trp
1               5                   10                  15

Val Lys Gln Asn Gln Gly Lys Ser Leu Glu Trp Ile Gly Glu Ile Asn
            20                  25                  30

Pro Asn Asn Gly Gly Thr Asp Tyr Thr Gln Lys Phe Lys Gly Lys Ala
            35                  40                  45

Thr Leu Thr Val Asp Lys Ser Ser Ser Thr Ala Tyr Met Glu Leu Arg
        50                  55                  60

Ser Leu Thr Ser Glu Asp Ser Ala Val Tyr Tyr Cys Val Arg Thr Arg
65                  70                  75                  80

Tyr Trp Gly Gln Gly Thr Thr Val Thr Val Ser Ser
            85                  90
```

IMMUNOGENIC MEMAPSIN 2 β-SECRETASE PEPTIDES AND METHODS OF USE

CROSS-REFERENCE TO RELATED APPLICATIONS

The present application claims benefit of priority to U.S. Provisional Application Ser. No. 61/074,468, filed Jun. 20, 2008, the entire contents of which are hereby incorporated by reference.

GOVERNMENT FUNDING

This invention was made with United States Government support under 5P20 RR015577, awarded by the National Institutes of Health. The United States Government has certain rights in the invention.

TECHNICAL FIELD

This application pertains to antibodies which specifically bind to immunogenic memapsin 2β-secretase peptides for use in the treatment of Alzheimer's disease and memapsin 2β-secretase disorders. The application also pertains to immunogenic compositions comprising memapsin 2β-secretase peptides and uses thereof.

BACKGROUND OF THE INVENTION

Scientific investigation during the last two decades has substantiated a prominent role for brain amyloid-β (Aβ) in the pathogenesis of Alzheimer's disease. Existing evidence supports the contention that Alzheimer's disease (AD) is initiated by an excess level of Aβ in the brain. The neurotoxicity of Aβ leads to the death of neurons, inflammation of the brain, dementia, and AD (Selkoe, 1999; Selkoe and Schenk, 2003). Since Aβ occupies such a central role in AD pathogenesis, the reduction of Aβ in the brain has become a major therapeutic strategy for AD.

Aβ is a 40- or 42-residue peptide generated from the degradation of β-amyloid precursor protein (APP), a membrane protein, by two proteases known as γ-secretase and β-secretase (also known as memapsin 2, the name recommended by IUBMB's Enzyme Nomenclature Commission, or BACE1). In this pathway, memapsin 2 initiates the APP cleavage; then the second cleavage by γ-secretase, a multi-protein complex, produces Aβ. An excess level of the neurotoxic Aβ in the brain over a long period of time leads to the death of neurons, brain inflammation and other harmful events that mark the progression of Alzheimer's disease (AD). Thus, these proteases are major therapeutic targets.

The molecular entity of γ-secretase has not yet been conclusively identified although it is clear that this activity is associated with a membrane protein complex consisting presenilin-1, nicastrin and others (Wolfe, 2002). β-secretase was cloned and identified as a membrane anchored aspartic protease called memapsin 2 (Lin et al., 2000; U.S. Pat. No. 6,545,127; PCT Publication No. WO 2007/021886). Four other laboratories independently discovered this enzyme and assigned different names for this protease: BACE (Vassar et al., 1999) and ASP-2 (Yan et al., 1999); Hussain et al, 1999). Memapsin 2β-secretase (also referred to as Memapsin 2, β-secretase, and/or BACE1) is a class I membrane protein that includes a protease domain highly homologous to pepsin, a transmembrane domain and a cytosolic domain. The protease is synthesized in vivo with an N-terminal pro-region, which is cleaved by furin to remove a 33-residue pro-segment en route to the cell surface (Capell et al., 2000). The crystal structure of memapsin 2 protease domain (Hong et al., 2000) shows that it contains an extended active-site cleft characteristic of aspartic proteases, and that the Aβ-hairpin flap covers over the active-site cleft. As in other aspartic proteases, the flap must open to permit the entering of substrate into the active-site cleft.

Memapsin 2 initiates cleavage of amyloid precursor protein (APP) leading to the production of Aβ and the onset of AD. The native APP is a poor substrate of memapsin 2 (Lin et al., 2000; Ermolieff et al., 2000). The so-called "Swedish mutation" of APP at the $P_2$-$P_1$ subsites from Lys-Met to Asn-Leu enhances the hydrolytic efficiency by about 60 fold, increases Aβ production and manifests an early onset form of AD. The specificity of all eight substrate residues has been determined (Turner et al., 2001). Native memapsin 2 is glycosylated by three N-linked oligosaccharides. The hinge which links the catalytic unit to the transmembrane region is only 6 residues (Hong et al., 2000). The transmembrane domain contains three cysteines which are covalently linked to palmitic acids. This is consistent with the lipid raft localization of memapsin 2 in the membranes. The intracellular domain contains a signal for endocytosis from cell surface to endosomes, which likely involve the recognition of proteins such as GGA for transport through the clathrin-coated vesicles (He et al., 2002). The optimal pH for memapsin 2 activity is about 4.5.

At present, there is no disease-modifying therapy for the clinical treatment of AD that has received regulatory approval. The few available drugs for treating AD are mostly acetylcholinesterase inhibitors, such as Donepezil (Aricept), which can only mildly improve cognitive performance and treats the symptoms of AD rather than the root cause of the disease. Therefore, there is an acute need for the development of new treatments for this disease.

Due to the current limitations of AD treatment regimes, there remains a significant interest in and need for additional or alternative therapies for treating, stabilizing, preventing, and/or delaying AD. The present invention fulfills this and other needs.

The specification is most thoroughly understood in light of the references cited herein. Each of these references is hereby incorporated by the reference in its entirety.

SUMMARY OF THE INVENTION

In one aspect, the present invention provides immunogenic compositions comprising one or more peptides of memapsin 2β-secretase.

In some embodiments, the invention provides immunogenic compositions comprising one or more peptides selected from the group consisting of KMDCKEYNYDKSIVDS-GTTNLRLPKK (SEQ ID NO:1), LRLPKKVFEAAVKSI-KAA (SEQ ID NO:2), RKGVYVPYTQGKWEGELGT-DLVSIPHGPNVTVRANI (SEQ ID NO:3), GLAYAEIA-RPDDSLEPFFDSLVKQTHVPNLFSLQLCGAGFPLNQS-EVLAS (SEQ ID NO:4), VEGPFVTLDMEDCGYNIPQT-DEST (SEQ ID NO:5), TDEEPEEPGRRGSFVEMVDNL-RGKSGQG (SEQ ID NO:6), and MGEVTNQSRFITI-LPQQYLRPVEDVATSQDDCYK (SEQ ID NO:7). In some embodiments, the one or more peptides are selected from the group KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3). In some embodiments, the peptide is KMD-CKEYNYDKSIVDSGTTNLRLPKK (SEQ ID NO:1). In some embodiments, the peptide is LRLPKKVFEAAVKSI- KAA (SEQ ID NO:2). In some embodiments, the peptide is RKGVYVPYTQGKWEGELGTDLVSIPHGPNVTVRANI (SEQ ID NO:3). In some embodiments, the peptide is GLAYAEIARPDDSLEPFFDSLVKQTHVPNLFSLQLCG-AGFPLNQSEVLAS (SEQ ID NO:4). In some embodiments, the peptide is VEGPFVTLDMEDCGYNIPQTDEST (SEQ ID NO:5). In some embodiments, the peptide is TDEEPEEPGRRGSFVEMVDNLRGKSGQG (SEQ ID NO:6). In some embodiments, the peptide is MGEVTNQSR-FITILPQQYLRPVEDVATSQDDCYK (SEQ ID NO:7).

In some embodiments, the one or more peptides specifically bind to a B-cell and/or T-cell surface antigen receptor. In some embodiments, one or more peptides specifically bind to an MHC class I or class II molecule.

In some embodiments, the immunogenic composition induces a Th1 response. In some embodiments, the immunogenic composition induces a Th2 response. In some embodiments, the Th2 response produces $IgG_1$ and/or $IgG_{2b}$ antibodies.

In some embodiments, the immunogenic composition reduces memapsin 2β-secretase activity. In some embodiments, the immunogenic composition selectively reduces memapsin 2 catalytic activity relative to memapsin 1 catalytic activity. In some embodiments, the immunogenic composition selectively reduces memapsin 2 catalytic activity relative to cathepsin D catalytic activity. In some embodiments, the immunogenic composition reduces memapsin 2 catalytic activity by at least about 10-fold more than memapsin 1 catalytic activity. In some embodiments, the immunogenic composition reduces memapsin 2 catalytic activity by at least about 10-fold more than cathepsin D catalytic activity. In some embodiments, the immunogenic composition blocks the interaction between memapsin 2 and APP.

In some embodiments, the present invention also provides antibodies that specifically bind to one or more immunogenic peptides of memapsin 2β-secretase.

The invention provides antibodies which specifically bind to one or more peptides selected from the group consisting of KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTH-VPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVED-VATSQDDCYK (SEQ ID NO:7). In some embodiments, the antibodies specifically bind to one or more peptides selected from the group KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGP-NVTVRANI (SEQ ID NO:3). In some embodiments, the antibodies specifically bind to the peptide KMDCKEYNY-DKSIVDSGTTNLRLPKK (SEQ ID NO:1). In some embodiments, the antibodies specifically bind to the peptide LRLPKKVFEAAVKSIKAA (SEQ ID NO:2). In some embodiments, the antibodies specifically bind to the peptide RKGVYVPYTQGKWEGELGTDLVSIPHGPNVTVRANI (SEQ ID NO:3). In some embodiments, the antibodies specifically bind to the peptide GLAYAEIARPDDSLEPFFD-SLVKQTHVPNLFSLQLCGAGFPLNQSEVLAS (SEQ ID NO:4). In some embodiments, the antibodies specifically bind to the peptide VEGPFVTLDMEDCGYNIPQTDEST (SEQ ID NO:5). In some embodiments, the antibodies specifically bind to the peptide TDEEPEEPGRRGSFVEM-VDNLRGKSGQG (SEQ ID NO:6). In some embodiments, the antibodies specifically bind to the peptide MGEVTNQS-RFITILPQQYLRPVEDVATSQDDCYK (SEQ ID NO:7).

In some embodiments, the antibody is an $IgG_1$ and/or $IgG_{2b}$ isotype antibody. In particular embodiments, the antibody is an $IgG_1$ isotype antibody. In some embodiments, the antibody is an $IgG_{2b}$ isotype antibody. In some embodiments, the antibody is a polyclonal antibody, monoclonal antibody, antigen-binding antibody fragment, or single-chain antibody. In some embodiments, the antibody is a monoclonal antibody. In some embodiments, the monoclonal antibody is a chimeric antibody, humanized antibody, or human antibody. In some embodiments, the antibody fragment is a Fab, Fab', F(ab')$_2$, or Fv fragment. In some embodiments, the antibody fragment is a $V_{HH}$ single domain antibody. In particular embodiments, the antibody has light and heavy chain pairs selected from the group consisting of SEQ ID NOS: 9 and 11; SEQ ID NOS: 13 and 15; SEQ ID NOS: 17 and 19; SEQ ID NOS: 21 and 23; SEQ ID NOS: 27 and 29; SEQ ID NOS: 31 and 32; SEQ ID NOS: 33 and 34; and SEQ ID NOS: 35 and 36.

In some embodiments, the antibody has an affinity for memapsin 2 at least about 25 times greater than affinity for memapsin 1. In some embodiments, the antibody has an affinity for memapsin 2 at least about 25 times greater than affinity for cathepsin D. In some embodiments, the antibody reduces memapsin 2β-secretase activity. In some embodiments, the antibody selectively reduces memapsin 2 catalytic activity relative to memapsin 1 catalytic activity. In some embodiments, the antibody selectively reduces memapsin 2 catalytic activity relative to cathepsin D catalytic activity. In some embodiments, the antibody reduces memapsin 2 catalytic activity by at least about 10-fold more than memapsin 1 catalytic activity. In some embodiments, the antibody reduces memapsin 2 catalytic activity by at least about 10-fold more than cathepsin D catalytic activity. In some embodiments, the antibody blocks the interaction between memapsin 2 and APP.

The invention also provides host cells comprising the polynucleotides and vectors described herein. The invention further provides methods for producing any of the antibodies described herein. The methods may comprise the step of expressing one or more polynucleotides encoding the antibody (which may be separately expressed as a single heavy or light claim, or both heavy and light chains expressed from one vector) in a suitable host cell, e.g., cell line.

In some embodiments, the invention also provides pharmaceutical compositions comprising one or more of the antibodies and/or immunogenic compositions described herein and a pharmaceutically acceptable excipient.

The invention also provides kits comprising one or more of the antibodies and/or immunogenic compositions described herein and instructions for use or disposal of reagents in the kit.

The invention further provides methods of detecting memapsin 2β-secretase using one or more of the antibodies and/or immunogenic compositions described herein. In some embodiments, the invention provides methods of detecting memapsin 2β-secretase in a cell, tissue, fluid, or sample, comprising contacting the cell, tissue, fluid or sample containing memapsin 2β-secretase with an antibody and/or immunogenic composition as described herein. In some embodiments, the invention provides methods of detecting memapsin 2β-secretase in in vitro assays as described herein.

In some embodiments, the invention provides methods of reducing memapsin 2β-secretase activity to treat a disease associated with memapsin 2β-secretase activity in a subject in need thereof, the method comprising administering to said subject an effective amount of one or more of the antibodies or peptides described herein. In some embodiments, the antibody is an antibody which specifically binds to one or more peptides, or is a peptide, selected from the group consisting of KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTH-VPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVED-VATSQDDCYK (SEQ ID NO:7).

In some embodiments, the invention provides methods of decreasing levels of β-amyloid peptide in the brain of a subject, said method comprising administering to said subject an effective amount of one or more of the antibodies or peptides described herein. In some embodiments, the antibody is an antibody which specifically binds to one or more peptides, or is a peptide, selected from the group consisting of KMDCK-EYNYDKSIVDSGTTNLRLPKK (SEQ ID NO:1), LRLP-KKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTH-VPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVED-VATSQDDCYK (SEQ ID NO:7).

The invention also provides methods of reducing the size or number of β-amyloid plaques in the brain of said subject, said method comprising administering to said subject an effective amount of one or more of the antibodies or peptides described herein. In some embodiments, the antibody is an antibody which specifically binds to one or more peptides, or is a peptide, selected from the group consisting of KMDCKEY-NYDKSIVDSGTTNLRLPKK (SEQ ID NO:1), LRLP-KKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTH-VPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVED-VATSQDDCYK (SEQ ID NO:7).

The invention further provides methods of treating Alzheimer's disease in a patient in need thereof, said method comprising administering to said subject an effective amount of one or more of the antibodies or peptides described herein. In some embodiments, the antibody is an antibody which specifically binds to one or more peptides, or is a peptide, selected from the group consisting of KMDCKEYNYDK-SIVDSGTTNLRLPKK (SEQ ID NO:1), LRLP-KKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTH-VPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVED-VATSQDDCYK (SEQ ID NO:7).

In another embodiment of the invention is provided use of the antibodies or peptides in accordance with the methods described herein. For example, in some embodiments are provided use of the antibodies as described herein for reducing the levels of β-amyloid peptide, as described herein. In other embodiments are provided use of the antibodies or peptides described herein for inhibiting memapsin 2β-secretase activity as described herein.

In a further aspect of the invention is provided use of the antibodies or peptides as described herein in the manufacture of a medicament. Particularly, the manufacture of a medicament for use in the treatment and/or prevention of conditions as described herein. Further, the formulations thereof, variously described herein are also intended for use in the manufacture of a medicament for use in treatment and/or prevention of the conditions and, in accordance with the methods, described herein, unless clearly dictated otherwise by context or specifically noted.

It is to be understood that one, some, or all of the properties of the various embodiments described herein may be combined to form other embodiments of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 depicts the amino acid sequence of pet11a-M2. Amino acids are numbered above the sequence from 1 to 393 for amino acids corresponding to the mature protease domain of memapsin 2, numbering from the pepsin mature amino terminus. Amino acid residues −63 to −49 correspond to vector-encoded T7 leader peptide, and amino acid residues −48 to −1 correspond to memapsin 2 pro-peptide. Numbering beneath the sequence in italic font corresponds to linear contiguous numbering from 1 to 456 to correspond to SEQ ID NO:8. Underlined sequence from −21 to 393 depicts region selected for epitope mapping.

FIG. 2 depicts overlapping decapeptide sets synthesized on polystyrene pins for sequence epitope mapping of memapsin 2. Each decapaptide is derived from the amino acid sequence of memapsin 2, amino acid residues −21 to 393, as numbered in FIG. 1 (residues 43 to 456 of SEQ ID NO:8), and overlaps by 8 amino acids. The 203 overlapping decapeptides represent the entire memapsin 2 sequence depicted below the pin sequences, numbered sequentially above, and by SEQ ID NO:8 numbers below (with section removed for clarity) as underlined in FIG. 1.

Figure 3:
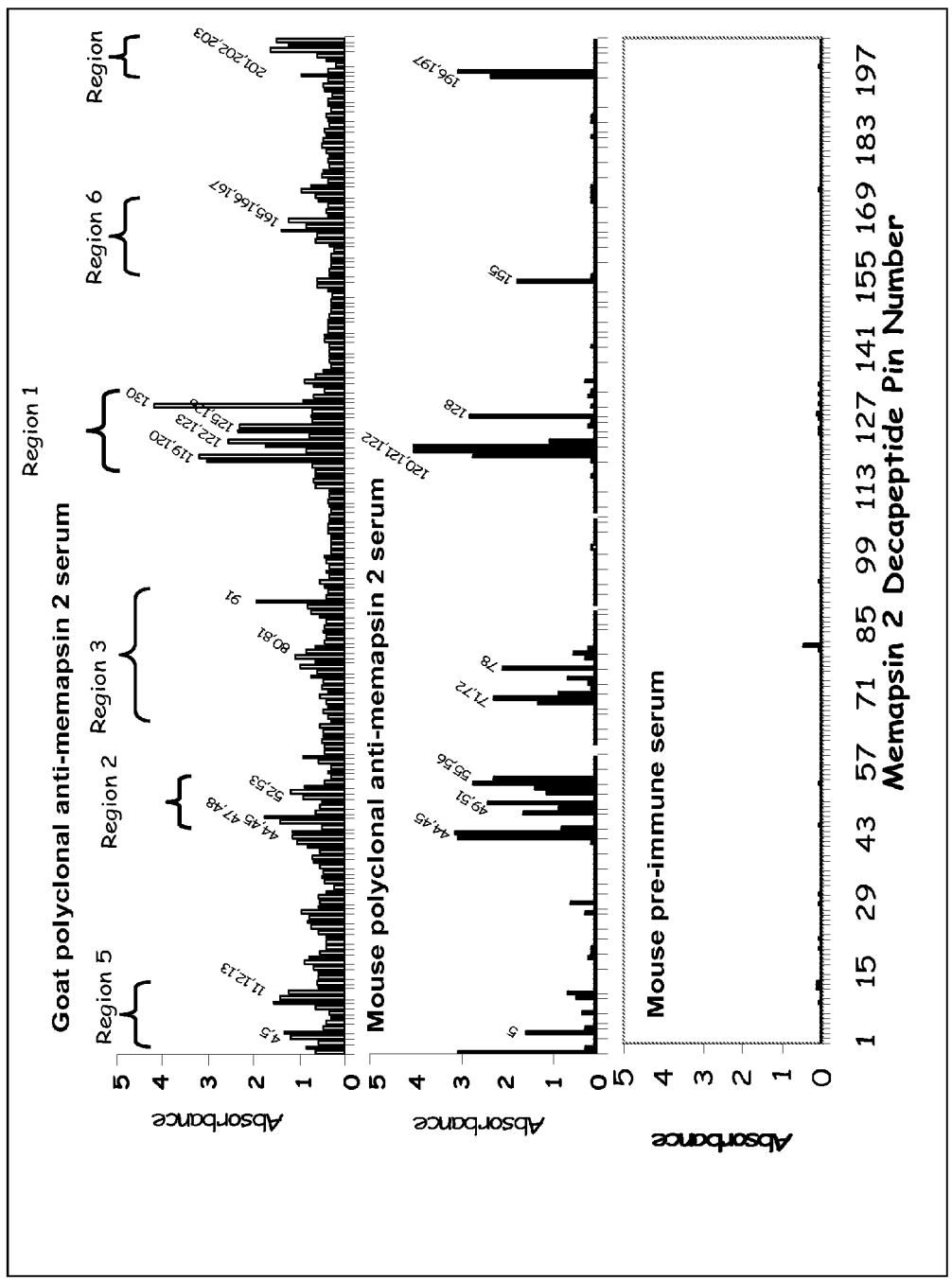
FIG. 3 depicts memapsin 2 epitope mapping solid-phase pin ELISA shows similar epitopes of recognition for goat and mouse polyclonal anti-memapsin 2 serum toward decapeptides derived from human memapsin 2 amino acid sequence. Overlapping memapsin 2 decapeptides were synthesized and immobilized on polystyrene pins, numbering from 1 to 203, as illustrated in FIG. 2. Pre-immune serum shows very little immunoreactivity (bottom panel). Immunoreactive pins are highlighted by number in the panels with results from goat and mouse anti-memapsin 2 binding. Brackets denote approximate location of regions of immunoreactivity common to both mouse and goat anti-memapsin 2, numbered in order of intensity of absorbance in solid-phase pin ELISA (Table 2). Common clusters of contiguous overlapping immunoreactive decapeptides were combined into regions if fewer than 5 amino acids separated the C-terminus of the previous cluster decapeptide with the N-terminus of the following cluster decapeptide.

FIG. 4 depicts clusters of common immunoreactivity of anti-memapsin 2 immune sera from mice and goats, mapped onto the memapsin 2 sequence. Clusters of overlapping decapeptides are underlined in the human memapsin 2 sequence (FIG. 1). Results of solid-phase pin ELISA common to both immune sera were collected into regions of interest (double-underlined sequence). Regions are numbered and prioritized by intensity of signal in the assay (FIG. 3 and Table 2).

FIG. 5 depicts the design of human memapsin 2 oligopeptides representing clusters of immunoreactivity common to both mouse and goat anti-memapsin 2 sera. Oligopeptides of length approximately 10-25 amino acids are preferred for optimal immunoreactivity as antigens and limitations of peptide synthesis. Therefore Region 1 was subdivided into two sequences for synthesis of oligopeptides representing the major region of common immunoreactivity (peptides named #1-a (SEQ ID NO: 1) and 1-b (SEQ ID NO: 2)). Region 2 peptide is designated as #2 (SEQ ID NO: 3). Beginning and end of immunoreactive regions are numbered beneath their respective amino acid sequences, in the scheme of the mature protease domain, numbering from the amino terminus of the homolog pepsin (FIG. 1).

FIG. 6 depicts the amino acid sequences of two essential epitopes (SEQ ID NOS: 1 and ?) used in immunization and monoclonal antibody generation.

Figure 7:
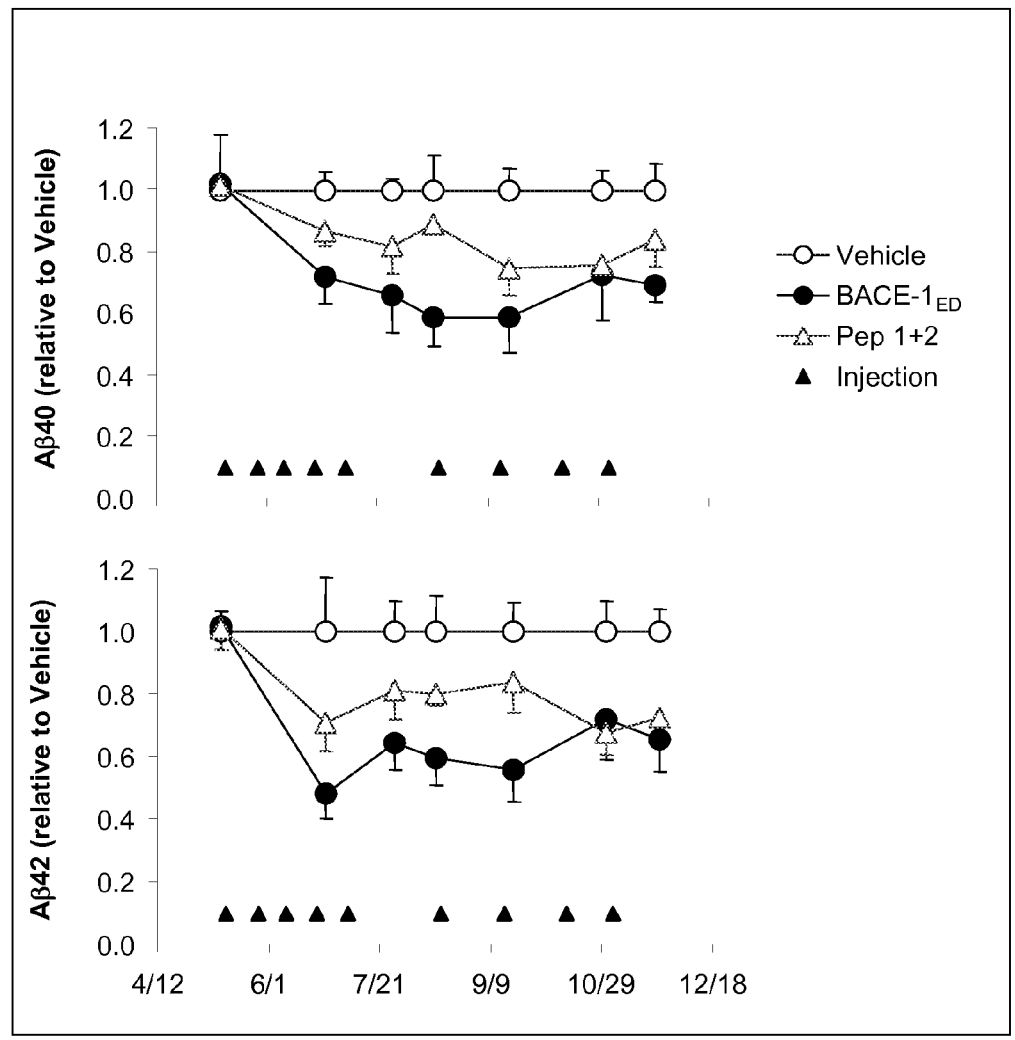

FIG. 7 depicts effect of memapsin $2_{ED}$ or Peptide 1a and 2a (Pep 1+2) active immunization on plasma $A\beta_{40}$ and $A\beta_{42}$ concentrations in young AD mice. Transgenic Tg2576 mice (n=4, 4-month-old) were subcutaneously injected with PBS or 30 μg of memapsin $2_{ED}$ or KLH-conjugated peptides 1a and 2a (FIG. 6) in 100 μl of volume for 7 months (see arrows). The study regimen was relatively followed the previous published manuscript (Chang et al., 2007). Concentrations of plasma Aβ were determined by sandwich ELISA. Data shown are from 1 of 3 independent experiments.

Figure 8:
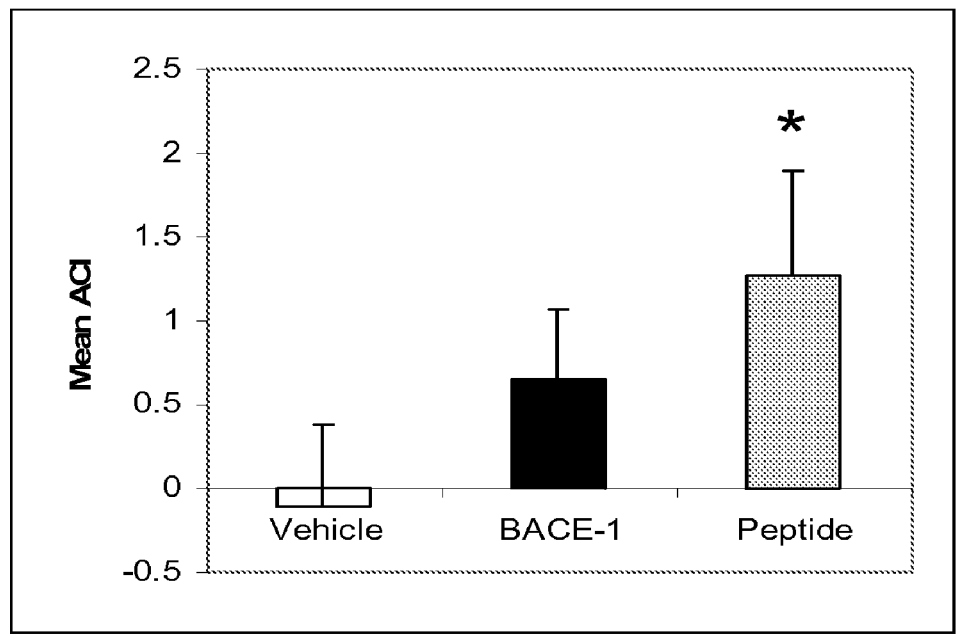

FIG. 8 depicts the effect of immunization with memapsin $2_{ED}$ or peptide 1a and 2a (FIG. 6) as assessed in a reference-memory version of MWM. Spatial memory as evaluated by annulus crossing index (ACI) during probe trials administered in the beginning of training days 3 and 5. Peptide 1a and 2a (FIG. 6) immunized mice ("Peptide") showed a significantly higher ACI for platform location whereas PBS control mice show a reduced (negative) ACI (asterisk p<0.05).

Figure 9:
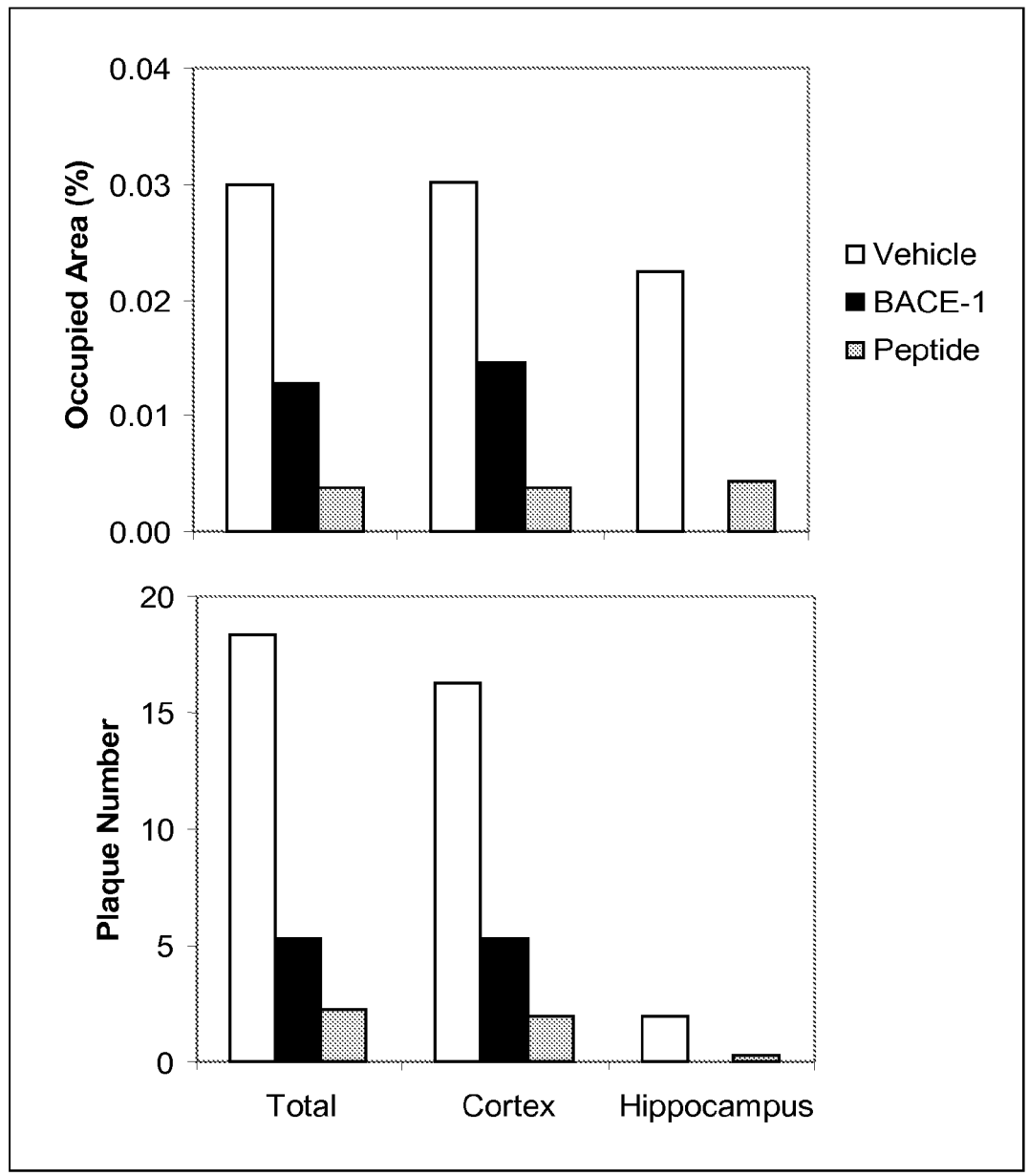

FIG. 9 depicts the effect of memapsin 2 and peptide 1a and 2a (FIG. 6) immunization on amyloid load in Tg2576 brains. Both occupied areas and amyloid plaque numbers were markedly decreased in brains with memapsin 2 or peptide 1a and 2a ("Peptide") immunization in the cortex, hippocampus, and total areas.

Figure 10:
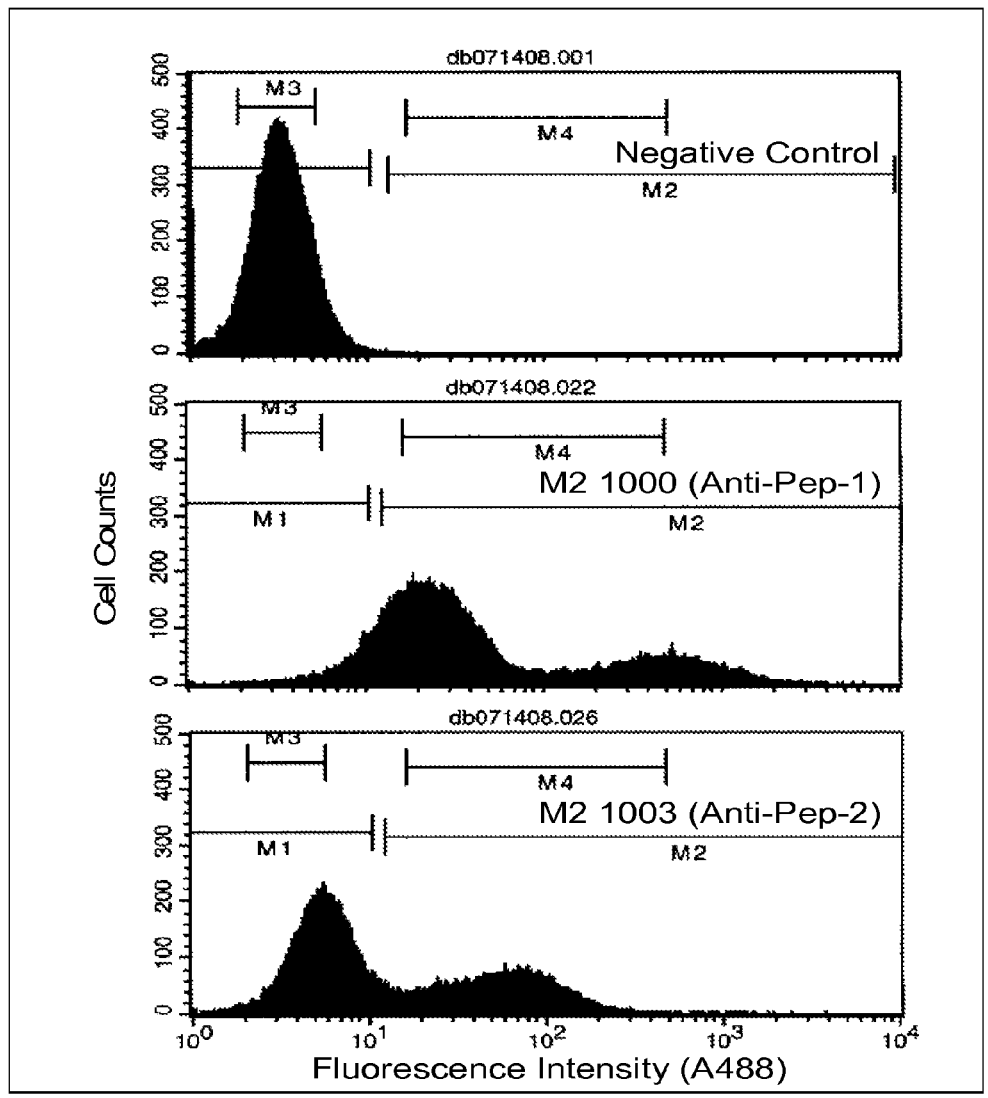

FIG. 10 depicts the cell surface memapsin 2 binding ability by monoclonal antibodies (mAb) M2 1000 and M2 1003, specific to peptides 1a and 2a respectively (FIG. 6), determined by flow cytometry analysis. Murine neuroblastoma CAD cells were transiently transfected with human memapsin 2 by FuGene (Roche). The transfected CAD cells were labeled with mAb followed by Alexa 488 conjugated secondary antibody. The negative control shows the basal level of fluorescence intensity from CAD and the secondary antibody only. The mAb (M2 1000 or M2 1003) labeled cells demonstrated a higher fluorescent small peak (to the right) and a lower fluorescent large peak (to the left) indicating the memapsin 2-transfected CAD expressing the higher levels versus the untransfected cells expressing the endogenous memapsin 2, respectively.

Figure 11:
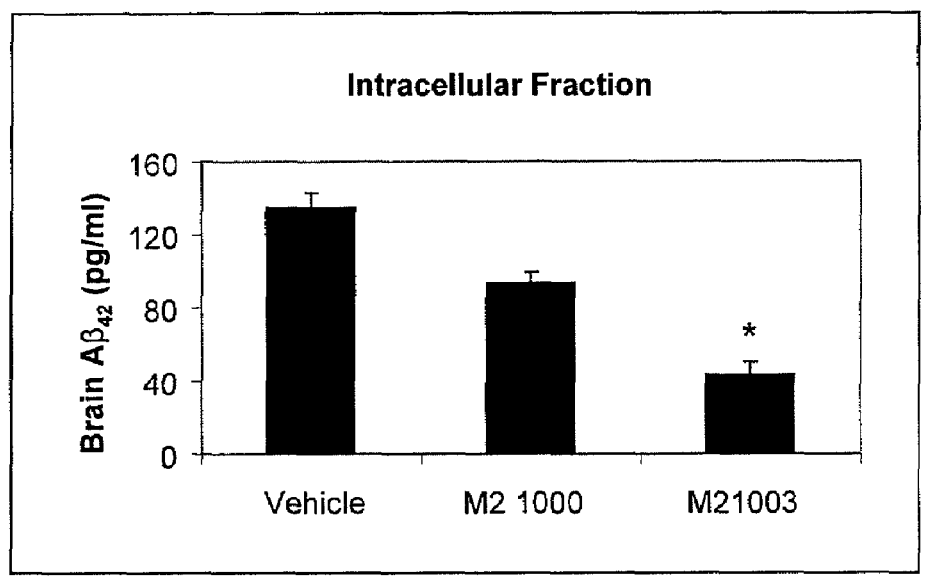

FIG. 11 depicts brain Aβ reduction by a direct administration of monoclonal antibodies MW 1000 and M2 1003 to the hippocampal area of mouse brains for 28 days. Aβ42 concentrations were determined by sandwich ELISA (asterisk p<0.05).

FIGS. 12A-B shows a comparison of light (FIG. 12A) and heavy (FIG. 12B) chain variable regions for eight monoclonal antibodies. The CDRs are underlined and are in the order CDR1, CDR2 and CD3, left to right in the sequences. * indicates a stop codon.

FIG. 13 shows nine monoclonal antibodies specifically against the essential antigenic epitopes of memapsin 2 determined by solid-phase anti-peptide ELISA. One epitope (Pep-1 between amino acid 214 and 239) indicates the β-sheet secondary structure which are located on top of the active cleft. The other epitope (Pep-2 between amino acid 64 and 79) is the hair pin flap partially covering the active site. The isotype, epitope, and titer (against the ectodomain of human memapsin 2, $hM2_{ED}$) of each monoclonal antibody are determined by ELISA (n.a. not available).

Figure 14:
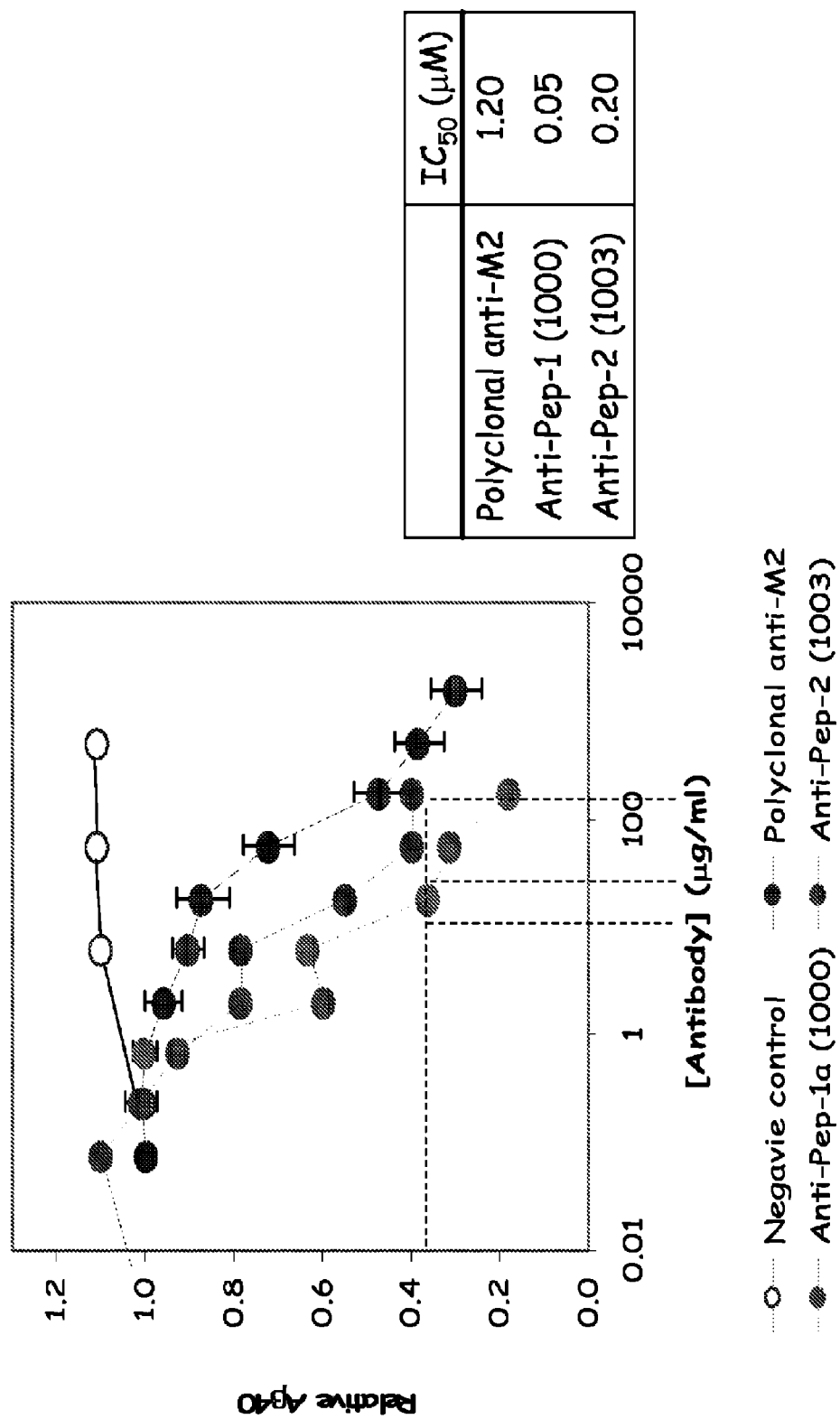

FIG. 14 shows inhibition of Aβ40 in cultured cells by affinity purified anti-memapsin 2 antibodies. Polyclonal goat anti-memapsin 2 antibodies (against the whole ectodomain) and monoclonal anti-peptide antibodies were purified and incubated with N2a cells stably transfected with amyloid precursor protein APP) Swedish mutant. The presence of Aβ40 in the overnight cultured supernatants was determined by sandwich ELISA (Invitrogen) and $IC_{50}$ values were calculated (GraFit v5.0).

DETAILED DESCRIPTION OF THE INVENTION

In certain aspects, the invention provides methods, compositions, unit dosages, and kits comprising immunogenic compositions comprising memapsin 2β-secretase peptides. The invention further provides methods, compositions, unit dosages, and kits comprising an antibody which specifically binds to immunogenic memapsin 2β-secretase peptides. The invention provides methods for reducing memapsin 2β-secretase activity to treat a disease associated with memapsin 2β-secretase activity and methods for decreasing levels of β-amyloid peptide and/or reducing the size or number of β-amyloid plaques in the brain of a subject comprising administering to the subject a therapeutically effective amount of an antibody which specifically binds to immunogenic memapsin 2β-secretase peptides. Further, the invention provides methods for treating Alzheimer's disease in a patient comprising administering to the subject a therapeutically effective amount of an antibody which specifically binds to immunogenic memapsin 2β-secretase peptides.

I. Definitions

It should be noted that, as used herein, the singular form "a", "an", and "the" includes plural references unless indicated otherwise.

As used herein, the term "native" is meant to naturally occurring, i.e., is obtainable in nature.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains. Where applicable, and as will be understood by the skilled artisan, salts of peptides and oligopeptides are also included.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, '-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, variations wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), domain antibodies, and mutants thereof, fusion proteins comprising an antibody portion, and any other modified configuration of the immunoglobulin molecule that comprises an antigen recognition site. An antibody includes an antibody of any class, such as IgG, IgA, or IgM (or subclass thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition.

The terms variable light chain ($V_L$) and variable heavy chain ($V_H$) refer to these light and heavy chains respectively. References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv, or Fab.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see FUNDAMENTAL IMMUNOLOGY (1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., 1990), having antigen-binding capability (e.g., Fab', F(ab')$_2$, Fab, Fv and rIgG. See also, PIERCE CATALOG AND HANDBOOK, 1994-1995 (Pierce Chemical Co., Rockford, Ill.). See also, e.g., Kuby (1998). The term antibody also includes bivalent or bispecific molecules, diabodies, triabodies, and tetrabodies. Bivalent and bispecific molecules are described in, e.g., Kostelny et al. (1992); Pack and Pluckthun, *Biochemistry* (1992); Zhu et al. (1997); Hu et al. (1996); Adams et al. (1993); and McCartney et al. (1995).

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein (1975) (incorporated by reference in its entirety), or may be made by recombinant DNA methods such as described in U.S. Pat. No. 4,816,567 (incorporated by reference in its entirety). The monoclonal antibodies may also be isolated from phage libraries generated using the techniques described in McCafferty et al. (1990) (incorporated by reference in its entirety), for example.

As used herein, "humanized" antibodies refer to forms of non-human (e.g., murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996; Sheets et al., 1998; Hoogenboom and Winter, 1991; Marks et al., 1991). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., (1985); Boemer et al., (1991); and U.S. Pat. No. 5,750,373.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., 1991, National Institutes of Health, Bethesda Md.); and (2) an approach based on crystallographic studies of antigen-antibody complexes (Al-lazikani et al. (1997)). As used herein, a CDR may refer to CDRs defined by either approach or by a combination of both approaches.

A "constant region" of an antibody refers to the constant region of the antibody light chain or the constant region of the antibody heavy chain, either alone or in combination.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An epitope that "specifically binds" to an antibody or a polypeptide is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances. For example, an antibody that specifically or preferentially binds to a memapsin 2β-secretase epitope is an antibody that binds this epitope with greater affinity, avidity, more readily, and/or with greater duration than it binds to other memapsin 2β-secretase epitopes or non-memapsin 2β-secretase epitopes. It is also understood by reading this definition that, for example, an antibody (or moiety or epitope) that specifically binds to a first target may or may not specifically bind to a second target. As such, "specific binding" does not necessarily require (although it can include) exclusive binding. Generally, but not necessarily, reference to binding means preferential binding.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., EPITOPE MAPPING PROTOCOLS IN METHODS IN MOLECULAR BIOLOGY (1996).

The term "$k_{on}$", as used herein, is intended to refer to the on rate constant for association of an antibody to an antigen.

The term "$k_{off}$", as used herein, is intended to refer to the off rate constant for dissociation of an antibody from the antibody/antigen complex.

The term "$K_D$", as used herein, is intended to refer to the equilibrium dissociation constant of an antibody-antigen interaction.

An "immunogenic composition" is a composition that comprises one or more peptides wherein administration of the composition to a subject results in the development in the subject of a humoral and/or a cellular immune response to the peptide.

As used herein, "substantially pure" refers to material which is at least 50% pure (i.e., free from contaminants), more preferably at least 90% pure, more preferably at least 95% pure, more preferably at least 98% pure, more preferably at least 99% pure.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, an "effective dosage" or "effective amount" of a drug, compound, or pharmaceutical composition is an amount sufficient to effect beneficial or desired results. For prophylactic use, beneficial or desired results includes results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results includes clinical results such as inhibiting, suppressing or reducing the formation of amyloid plaques, reducing, removing, clearing amyloid plaques, improving cognition, reversing or slowing cognitive decline, reducing levels of β-amyloid peptide (including soluble, oligomeric and deposited), reducing or suppressing memapsin 2β-secretase activity, decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients.

An effective dosage can be administered in one or more administrations. For purposes of this invention, an effective dosage of a drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, one or more of the following: inhibiting, suppressing or reducing the formation of amyloid plaques, reducing, removing, or clearing amyloid plaques, improving cognition, reversing or slowing cognitive decline, inhibiting, slowing and/or reducing memapsin 2β-secretase activity, reducing levels of β-amyloid peptide, (including soluble, oligomeric and deposited) in a tissue (such as brain), inhibiting, slowing and/or reducing accumulation of Aβ peptide in the brain, decreasing symptoms resulting from the disease, increasing the quality of life of those suffering from the disease, decreasing the dose of other medications required to treat the disease, delaying the progression of the disease, and/or prolonging survival of patients. In some embodiments, the composition reduces the severity of one or more symptoms associated with disease by at least about any of 10%, 20%, 30%, 40%, 50%, 60%, 70%, 80%, 90%, 95% or 100% compared to the corresponding symptom in the same subject prior to treatment or compared to the corresponding symptom in other subjects not receiving the composition.

As used herein, "delaying" development of Alzheimer's disease means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects.

"Development" of Alzheimer's disease means the onset and/or progression of Alzheimer's disease within an individual. Alzheimer's disease development can be detectable using standard clinical techniques as described herein. However, development also refers to disease progression that may be initially undetectable. For purposes of this invention, progression refers to the biological course of the disease state, in this case, as determined by a standard neurological examination, or patient interview or may be determined by more specialized testing. A variety of these diagnostic tests include, but not limited to, neuroimaging, detecting alterations of levels of specific proteins in the serum or cerebrospinal fluid (e.g., amyloid peptides and Tau), computerized tomography (CT), and magnetic resonance imaging (MRI). "Development" includes occurrence, recurrence, and onset. As used herein "onset" or "occurrence" of Alzheimer's disease includes initial onset and and/or recurrence.

An "individual" or a "subject" is a mammal, more preferably a human. Mammals also include, but are not limited to, farm animals, sport animals, pets, primates, horses, dogs, cats, mice, and rats.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, REMINGTON'S PHARMACEUTICAL SCIENCES, 18$^{th}$ Ed., 1990; and REMINGTON, THE SCIENCE AND PRACTICE OF PHARMACY, 20$^{th}$ Ed., 2000).

Reference to "about" a value, a parameter or an amino acid position herein includes (and describes) embodiments that are directed to that value, parameter, or amino acid position per se.

It is understood that aspects and variations of the invention described herein include "consisting" and/or "consisting essentially of" aspects and variations.

II. Immunogenic Composition Comprising Memapsin 2 Peptides

The present invention also provides immunogenic compositions comprising one or more immunogenic peptides of memapsin 2β-secretase. In some embodiments, the immunogenic compositions comprise one or more peptides selected from the group consisting of KMDCKEYNYDKSIVDS-GTTNLRLPKK (SEQ ID NO:1), LRLPKKVFEAAVKSI-KAA (SEQ ID NO:2), RKGVYVPYTQGKWEGELGT-DLVSIPHGPNVTVRANI (SEQ ID NO:3), GLAYAEIARP-DDSLEPFFDSLVKQTHVPNLFSLQLCGAGFPLNQSEV-LAS (SEQ ID NO:4), VEGPFVTLDMEDCGYNIPQTD-EST (SEQ ID NO:5), TDEEPEEPGRRGSFVEMVDNL-RGKSGQG (SEQ ID NO:6), and MGEVTNQSR-FITILPQQYLRPVEDVATSQDDCYK (SEQ ID NO:7). In some embodiments, the one or more peptides are selected from the group KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGP-NVTVRANI (SEQ ID NO:3). In some embodiments, the peptide is KMDCKEYNYDKSIVDSGTTNLRLPKK (SEQ ID NO:1). In some embodiments, the peptide is LRLP-KKVFEAAVKSIKAA (SEQ ID NO:2). In some embodiments, the peptide is RKGVYVPYTQGKWEGELGTDLV-SIPHGPNVTVRANI (SEQ ID NO:3). In some embodiments, the peptide is GLAYAEIARPDDSLEPFFD-SLVKQTHVPNLFSLQLCGAGFPLNQSEVLAS (SEQ ID NO:4). In some embodiments, the peptide is VEG-PFVTLDMEDCGYNIPQTDEST (SEQ ID NO:5). In some embodiments, the peptide is TDEEPEEPGRRGSFVEM-VDNLRGKSGQG (SEQ ID NO:6). In some embodiments, the peptide is MGEVTNQSRFITILPQQYLRPVED-VATSQDDCYK (SEQ ID NO:7).

In some embodiments, the immunogenic composition reduces memapsin 2β-secretase activity. In certain embodiments, the immunogenic composition may reduce memapsin 2β-secretase activity by about any of 5%, 10%, 15%, 20%, 25%, 30%, 35%, 40%, 45%, 50%, 55%, 60%, 65%, 70%, or 75%. In some embodiments, the immunogenic composition may reduce memapsin 2β-secretase activity by between any of about 10-25%, about 10-50%, about 25-50%, or about 20-40%. In some embodiments, the immunogenic composition may reduce memapsin 2β-secretase activity by between about 10% and about 50%. In some embodiments, the immunogenic composition may reduce memapsin 2β-secretase activity by greater than any of about 10%, about 20%, about 30%, about 40%, about 50%, or about 60%.

In some embodiments, the immunogenic composition selective reduces memapsin 2 catalytic activity relative to memapsin 1 catalytic activity. The immunogenic composition reduces memapsin 2 catalytic activity by about any of 2-fold, 3-fold, 5-fold, 10-fold, or 15-fold more than memapsin 1 catalytic activity. In some embodiments, the immunogenic composition reduces memapsin 2 catalytic activity by at least any of about 2-fold, about 3-fold, about 5-fold, about 10-fold, or about 15-fold more than memapsin 1 catalytic activity. In some embodiments, the immunogenic composition reduces memapsin 2 catalytic activity by at least about 10-fold more than memapsin 1 catalytic activity. In some embodiments, the immunogenic composition reduces memapsin 2 catalytic activity by between any of about 2-fold to about 3-fold, about 2-fold to about 5-fold, about 2-fold to about 10-fold, or about 5-fold to about 10-fold more than memapsin 1 catalytic activity.

In some embodiments, the immunogenic composition selective reduces memapsin 2 catalytic activity relative to cathepsin D catalytic activity. The immunogenic composition reduces memapsin 2 catalytic activity by about any of 2-fold, 3-fold, 5-fold, 10-fold, or 15-fold more than cathepsin D catalytic activity. In some embodiments, the immunogenic composition reduces memapsin 2 catalytic activity by at least any of about 2-fold, about 3-fold, about 5-fold, about 10-fold, or about 15-fold more than cathepsin D catalytic activity. In some embodiments, the immunogenic composition reduces memapsin 2 catalytic activity by at least about 10-fold more than cathepsin D catalytic activity. In some embodiments, the immunogenic composition reduces memapsin 2 catalytic activity by between any of about 2-fold to about 3-fold, about 2-fold to about 5-fold, about 2-fold to about 10-fold, or about 5-fold to about 10-fold more than cathepsin D catalytic activity.

In some embodiments, the immunogenic composition blocks the interaction between memapsin 2 and APP.

In some embodiments, one or more peptides of the immunogenic composition specifically bind to a B-cell and/or T-cell surface antigen receptor. In some embodiments, one or more peptides of the immunogenic compositions specifically bind to an MHC class I or class II molecule. MHC class I or class II molecule binding is detectable using any assay known in the art such as flow cytometry.

In some embodiments, the immunogenic composition induces a Th1 response. In some embodiments, the immunogenic composition induces a Th2 response. In some embodiments, the Th2 response produces IgG$_1$ and/or IgG$_{2b}$ antibodies. In some embodiments, the Th2 response produces about any of 10%, 20%, 30%, 40%, 50%, 60%, 70%, or 80, IgG$_1$ and/or IgG$_{2b}$ antibodies, which specifically bind to one or more memapsin 2β-secretase peptides, of the total amount of antibodies, which specifically bind to one or more memapsin 2β-secretase peptides.

In some embodiments, the immunogenic composition further comprises an adjuvant. The adjuvant may induce a Th1 type and/or a Th2 type immune response. High levels of Th1-type cytokines (e.g., IFN-.gamma., TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. The levels of these cytokines may be readily assessed using standard assays. For a review of the families of cytokines, see Mosmann and Coffman (1989). Adjuvants which are capable of preferential stimulation of the Th1 cell response are described in International Patent Application No. WO 94/00153 and WO 95/17209 (incorporated by reference in their entirety).

III. Anti-Memapsin 2 Antibodies

The present invention also provides antibodies which specifically bind to one or more immunogenic peptides of memapsin 2β-secretase. In some embodiments, the antibodies which specifically bind to one or more immunogenic peptides of memapsin 2β-secretase are produced by administration of one or more of the immunogenic compositions described herein. In some embodiments, the antibodies specifically bind to one or more peptides selected from the group consisting of KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTHVPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVEDVATSQDDCYK (SEQ ID NO:7). In some embodiments, the antibodies specifically bind to one or more peptides selected from the group consisting of KMDCKEYNYDKSIVDSGTTNLRLPKK (SEQ ID NO:1), LRLPKKVFEAAVKSIKAA (SEQ ID NO:2), and RKGVYVPYTQGKWEGELGTDLVSIPHGPNVTVRANI (SEQ ID NO:3). In some embodiments, the antibodies specifically bind to the peptide KMDCKEYNYDKSIVDSGTTNLRLPKK (SEQ ID NO:1). In some embodiments, the antibodies specifically bind to the peptide LRLPKKVFEAAVKSIKAA (SEQ ID NO:2). In some embodiments, the antibodies specifically bind to the peptide RKGVYVPYTQGKWEGELGTDLVSIPHGPNVTVRANI (SEQ ID NO:3). In some embodiments, the antibodies specifically bind to the peptide GLAYAEIARPDDSLEPFFDSLVKQTHVPNLFSLQLCGAGFPLNQSEVLAS (SEQ ID NO:4). In some embodiments, the antibodies specifically bind to the peptide VEGPFVTLDMEDCGYNIPQTDEST (SEQ ID NO:5). In some embodiments, the antibodies specifically bind to the peptide TDEEPEEPGRRGSFVEMVDNLRGKSGQG (SEQ ID NO:6). In some embodiments, the antibodies specifically bind to the peptide MGEVTNQSRFITILPQQYLRPVEDVATSQDDCYK (SEQ ID NO:7).

In some embodiments of the antibodies as described herein, the antibody is an $IgG_1$ or $IgG_{2b}$ isotype antibody. In particular embodiments, the antibody is an $IgG_1$ isotype antibody. In some embodiments, the antibody is an $IgG_{2b}$ isotype antibody.

The antibodies of the invention are characterized by any (one or more) of the following characteristics: (a) ability to bind to memapsin 2β-secretase; (b) ability to reduce and/or inhibit memapsin 2β-secretase biological activity (s); (c) ability to reduce and/or inhibit APP cleavage; (d) ability to reduce and/or decrease levels of β-amyloid peptide in the brain; (e) ability to treat and/or prevent Alzheimer's disease; and (f) ability to reduce and/or decrease the size and/or number of β-amyloid plaques in the brain. Assays for the determination of these properties included those described herein and known to the skilled artisan, for example, such as those described in Chang et al. (2007) and Oddo et al. (2006), wherein β-amyloid plaques are revealed by immunohistochemical staining of tissue sections of brain tissue preserved in paraformaldehyde, followed by digital image analysis.

In some embodiments, the antibodies described herein specifically bind to immunogenic memapsin 2β-secretase peptides. Where the antibodies specifically bind to immunogenic memapsin 2β-secretase peptides, the antibodies may bind to the protein with a $K_D$ of less than about 0.1 mM, less than about 1 μM, less than about 0.1 μM, or less than about 0.01 μM. Specific polyclonal antisera and monoclonal antibodies may bind with a $K_D$ of less than about 0.1 mM, less than about 1 μM, less than about 0.1 μM, or less than about 0.01 μM. In some embodiments, the antibodies neutralize memapsin 2β-secretase activity.

In some embodiments, the antibody has greater affinity for memapsin 2 than affinity for memapsin 1. The antibody may have about any of 5, 10, 15, 20, 25, 30, 35, 45, or 50 times greater affinity for memapsin 2 than affinity for memapsin 1. In some embodiments, the antibody has an affinity for memapsin 2 at least about 25 times greater than affinity for memapsin 1.

In some embodiments, the antibody has greater affinity for memapsin 2 than affinity for cathepsin D. The antibody may have about any of 5, 10, 15, 20, 25, 30, 35, 45, or 50 times greater affinity for memapsin 2 than affinity for cathepsin D. In some embodiments, the antibody has an affinity for memapsin 2 at least about 25 times greater than affinity for cathepsin D.

In some embodiments, the antibody reduces memapsin 2β-secretase activity. The antibody may reduce memapsin 2β-secretase activity by about any of 5%, 10%, 15%, 20%, 25%, 30%, 35%, 40%, 45%, 50%, 55%, 60%, 65%, 70%, or 75%. In some embodiments, the antibody may reduce memapsin 2β-secretase activity by between any of about 10-25%, about 10-50%, about 25-50%, or about 20-40%. In some embodiments, the antibody may reduce memapsin 2β-secretase activity by between about 10% and about 50%. In some embodiments, the antibody may reduce memapsin 2β-secretase activity by greater than any of about 10%, about 20%, about 30%, about 40%, about 50%, or about 60%.

In some embodiments, the antibody selectively reduces memapsin 2 catalytic activity relative to memapsin 1 catalytic activity. The antibody reduces memapsin 2 catalytic activity by about any of 2-fold, 3-fold, 5-fold, 10-fold, or 15-fold more than memapsin 1 catalytic activity. In some embodiments, the antibody reduces memapsin 2 catalytic activity by at least any of about 2-fold, about 3-fold, about 5-fold, about 10-fold, or about 15-fold more than memapsin 1 catalytic activity. In some embodiments, the antibody reduces memapsin 2 catalytic activity by at least about 10-fold more than memapsin 1 catalytic activity. In some embodiments, the antibody reduces memapsin 2 catalytic activity by between any of about 2-fold to about 3-fold, about 2-fold to about 5-fold, about 2-fold to about 10-fold, or about 5-fold to about 10-fold more than memapsin 1 catalytic activity.

In some embodiments, the antibody selective reduces memapsin 2 catalytic activity relative to cathepsin D catalytic activity. The antibody reduces memapsin 2 catalytic activity by about any of 2-fold, 3-fold, 5-fold, 10-fold, or 15-fold more than cathepsin D catalytic activity. In some embodiments, the antibody reduces memapsin 2 catalytic activity by at least any of about 2-fold, about 3-fold, about 5-fold, about 10-fold, or about 15-fold more than cathepsin D catalytic activity. In some embodiments, the antibody reduces memapsin 2 catalytic activity by at least about 10-fold more than cathepsin D catalytic activity. In some embodiments, the antibody reduces memapsin 2 catalytic activity by between any of about 2-fold to about 3-fold, about 2-fold to about 5-fold, about 2-fold to about 10-fold, or about 5-fold to about 10-fold more than cathepsin D catalytic activity.

In some embodiments, the antibody blocks the interaction between memapsin 2 and APP.

In some embodiments, any of the antibodies described herein are a polyclonal antibody, monoclonal antibody, antigen-binding antibody fragment, or single-chain antibody. In some embodiments, any of the antibodies described herein are a monoclonal antibody. In some embodiments, the monoclonal antibody is a chimeric antibody, humanized antibody, or human antibody. In some embodiments, the antibody fragment is a Fab, Fab', F(ab')$_2$ or Fv fragment. In some embodiments, the antibody fragment is a V$_{HH}$ single domain antibody (nanobody).

The invention also provides methods of making any of these antibodies or polypeptides. The antibodies of this invention can be made by procedures known in the art (see, e.g., Coligan (1991); Harlow & Lane (1986); and Kohler & Milstein *Nature* (1975). A number of memapsin 2 oligopeptides comprising immunogens may be used to produce antibodies specifically reactive with immunogenic memapsin 2β-secretase and isotypes thereof. For example, the antibody may be generated by immunizing a mammal with a immunogenic composition comprising a memapsin 2β-secretase peptide as described herein. The polypeptides can be produced by proteolytic or other degradation of the antibodies, by recombinant methods (i.e., single or fusion polypeptides) or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415. Synthetic oligopeptides derived from the sequences disclosed herein, optionally conjugated to a carrier protein can be used as an immunogen. Either monoclonal or polyclonal antibodies may be generated, for subsequent use in immunoassays to measure or isolate the protein.

In another alternative, the antibodies can be made recombinantly using procedures that are well known in the art. Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., 1989; Ward et al., 1989). Antibodies are purified using techniques well known to those of skill in the art. The sequence encoding the antibody of interest may be maintained in a vector in a host cell and the host cell can then be expanded and frozen for future use. Vectors (including expression vectors) and host cells are further described herein.

Methods of preparing polyclonal antibodies are known to the skilled artisan. Polyclonal antibodies can be raised in a mammal, e.g., by one or more injections (e.g., subcutaneous or intraperitoneal injections) of a truncated memapsin 2 protein and, if desired, an adjuvant. For example, an inbred strain of mice (e.g., BALB/C mice) or rabbit may be immunized with the protein using an appropriate adjuvant and a standard immunization protocol. The animal's immune response to the immunogen preparation is monitored by taking test bleeds and determining the titer of reactivity to memapsin 2 oligopeptide. When appropriately high titers of antibody to the immunogen are obtained, blood is collected from the animal and antisera are prepared. Further fractionation of the antisera to enrich for antibodies reactive to the protein can be done if desired.

In some embodiments, the memapsin 2 peptide is conjugated to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal antibodies may be prepared using hybridoma methods, such as those described by Kohler & Milstein (1975). In a hybridoma method, a mouse, hamster, or other appropriate host animal, is typically immunized with a truncated memapsin 2 protein to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

The invention also encompasses single chain variable region fragments ("scFv") of antibodies of this invention. Single chain variable region fragments are made by linking light and/or heavy chain variable regions by using a short linking peptide. Bird et al. (1988). An example of a linking peptide is (GGGGS)$_3$ (SEQ ID NO: ?), which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which V$_H$ and V$_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al, 1993; Poljak et al., 1994).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986). Traditionally, the recombinant production of bispecific antibodies was based on the coexpression of two immunoglobulin heavy chain-light chain pairs, with the two heavy chains having different specificities (Millstein and Cuello, 1983).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of an antibody which bind specifically to an immunogenic memapsin 2β-secretase peptide fragment or one or more CDRs derived from an antibody which bind specifically to an immunogenic memapsin 2β-secretase peptide fragment can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; 5,225,539; 6,548,640.

In the recombinant humanized antibodies, the Fcγ portion can be modified to avoid interaction with Fcγ receptor and the complement immune system. This type of modification was designed by Dr. Mike Clark from the Department of Pathology at Cambridge University, and techniques for preparation of such antibodies are described in WO 99/58572, published Nov. 18, 1999.

For example, the constant region may be engineered to more resemble human constant regions to avoid immune response if the antibody is used in clinical trials and treatments in humans. See, for example, U.S. Pat. Nos. 5,997,867 and 5,866,692.

Human antibodies can be produced using various techniques known in the art, including phage display libraries (Hoogenboom & Winter, 1991; Marks et al., 1991). The techniques of Cole et al. and Boemer et al are also available for the preparation of human monoclonal antibodies (Cole et al., 1985 and Boerner et al., 1991). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. (1992); Lonberg et al. (1994); Morrison (1994); Fishwild et al. (1996); Neuberger (1996); Lonberg & Huszar (1995).

Antibodies may be collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against memapsin 2 oligopeptide or, using a competitive binding immunoassay.

Immunogenic memapsin 2β-secretase peptide specific antibodies allow for the detection of memapsin 2 protein by a variety of immunoassay methods. For a review of immunological and immunoassay procedures, see *Basic and Clinical Immunology* (1991). Moreover, the immunoassays can be performed in any of several configurations, which are reviewed extensively in *Enzyme Immunoassay* (1980); and Harlow & Lane, supra.

Binding affinity for immunogenic memapsin 2β-secretase peptide antibodies is typically measured or determined by standard antibody-antigen assays, such as Biacore competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen may be indicated by reference to the dissociation constant ($K_D=1/K$, where K is the affinity constant=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex). Typically, the binding interactions between antigen and antibody include reversible noncovalent associations such as electrostatic attraction, Van der Waals forces and hydrogen bonds.

Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to memapsin 2 oligopeptides or to cells expressing memapsin 2 oligopeptides on their surface are expanded in E. coli and subjected to another round of panning. In this way, an enrichment of many fold occurs in 3 rounds of panning. Thus, even when enrichment in each round is low, multiple rounds of panning will lead to the isolation of rare phage and the genetic material contained within which encodes the scFv with the highest affinity or one which is better expressed on phage.

Regardless of the method of panning chosen, the physical link between genotype and phenotype provided by phage display makes it possible to test every member of a cDNA library for binding to antigen, even with large libraries of clones.

The invention encompasses modifications to antibodies which specifically bind to an immunogenic memapsin 2β-secretase peptide, including functionally equivalent antibodies which do not significantly affect their properties and variants which have enhanced or decreased activity and/or affinity. For example, amino acid sequence of an antibody which specifically binds to an immunogenic memapsin 2β-secretase peptide may be mutated to obtain an antibody with the desired binding affinity to memapsin 2β-secretase. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

| Amino acid substitutions | | |
|---|---|---|
| Original Residue | Conservative Substitutions | Exemplary Substitutions |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997; Wright and Morrison, 1997). The oligosaccharide side chains of the immunoglobulins affect the protein's function (Boyd et al., 1996; Wittwe and Howard, 1990) and the intramolecular interaction between portions of the glycoprotein, which can affect the conformation and presented three-dimensional surface of the glycoprotein (Hefferis and Lund, supra; Wyss and Wagner, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999).

Other methods of modification include using coupling techniques known in the art, including, but not limited to, enzymatic means, oxidative substitution and chelation. Modifications can be used, for example, for attachment of labels for immunoassay. Modified memapsin 2β-secretase polypeptides are made using established procedures in the art and can be screened using standard assays known in the art, some of which are described below and in the Examples.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., 1992; Barbas et al., 1994; Schier et al., Gene, 1995; Yelton et al., 1995; Jackson et al., 1995; Hawkins et al, 1992; and WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased or no binding are identified. Methods for determining binding affinity are well-known in the art. Binding affinity may be determined using BIAcore surface plasmon resonance analysis, which detects differences in binding affinity of about 2-fold or greater. BIAcore is particularly useful when the starting antibody already binds with a relatively high affinity, for example a $K_D$ of about 10 nM or lower. Screening using BIAcore surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods. This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al. (1993).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acid (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using BIAcore surface plasmon resonance analysis, and selection using any method known in the art for selection, including phage display, yeast display, and ribosome display.

IV. Polynucleotides, Vectors, and Host Cells

The invention also provides isolated polynucleotides encoding the antibodies, polypeptides and peptides described herein and vectors and host cells comprising the polynucleotide. In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

An exemplary algorithm that is suitable for determining percent sequence identity and sequence similarity are the BLAST and BLAST 2.0 algorithms, which are described in Altschul et al. (1977) and Altschul et al. (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (world-wide-web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, 1989) alignments (B) of 50, expectation (E) of 10, M=5, N=-4, and a comparison of both strands.

The BLAST algorithm also performs a statistical analysis of the similarity between two sequences (see, e.g., Karlin & Altschul, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

In particular, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v)

formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195; 4,800,159; 4,754,065; and 4,683,202, as well as PCR: THE POLYMERASE CHAIN REACTION (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as $E.\ coli$ or $B.\ subtillis$) and yeast (such as $S.\ cerevisae,\ S.\ pombe$; or $K.\ lactis$). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to memapsin 2β-secretase is effected by an immunoassay or FACS. A cell overexpressing the antibody or protein of interest can be identified.

V. Pharmaceutical Compositions

The antibodies, peptides, polypeptides and polynucleotides described herein can be formulated into pharmaceutical compositions which are in a form suitable for administration to a patient. Suitable carriers and their formulations are described in REMINGTON'S PHARMACEUTICAL SCIENCES, 1990; and REMINGTON, THE SCIENCE AND PRACTICE OF PHARMACY, 2000. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

In some embodiments, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following excipients: carrier proteins such as serum albumin; buffers; fillers such as microcrystalline cellulose, lactose, corn and other starches; binding agents; sweeteners and other flavoring agents; coloring agents; and polyethylene glycol.

The compositions for administration will commonly comprise an antibody or peptide of the invention dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., REMINGTON'S PHARMACEUTICAL SCIENCE (1980) and Goodman & Gillman, (996).

The pharmaceutical compositions can be formulated for administration in a variety of unit dosage forms. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The pharmaceutical compositions for use in any of the methods described herein, whether in the context of use as a medicament and/or use for manufacture of a medicament.

Also provided are articles of manufacture and unit dosages comprising the compositions and formulations described herein for use in the methods of treatment, and methods of administration, and dosage regimes described herein. Suitable packaging for compositions and formulations described herein are known in the art, and include, for example vials (such as sealed vials), vessels (such as sealed vessels), ampules, bottles, jars, flexible packaging (e.g., sealed Mylar or plastic bags), and the like. These unit dosages and articles of manufacture may further be sterilized and/or sealed.

VI. Methods of Detection Memapsin 2β-Secretase

The present invention also includes, in some embodiments, methods of detection of memapsin 2β-secretase using the immunogenic compositions and memapsin 2β-secretase antibodies described herein. In some embodiments, the invention provides methods of detecting memapsin 2β-secretase in a cell, tissue, fluid, or sample comprising contacting the cell, tissue, fluid, or sample containing memapsin 2β-secretase with an antibody and/or immunogenic composition as described herein. In some embodiments, the invention provides methods of detecting memapsin 2β-secretase in in vitro assays using the immunogenic compositions and memapsin 2β-secretase antibodies described herein. Immunogenic compositions and memapsin 2β-secretase peptide specific antibodies allow for the detection of memapsin 2 protein by a variety of immunoassay methods. For a review of immunological and immunoassay procedures, see BASIC AND CLINICAL IMMUNOLOGY (1991). Moreover, the immunoassays can be performed in any of several configurations, which are reviewed extensively in ENZYME IMMUNOASSAY (1980). See also METHODS IN CELL BIOLOGY: ANTIBODIES IN CELL BIOLOGY (93); BASIC AND CLINICAL IMMUNOLOGY (1991).

Immunological binding assays (or immunoassays) typically use an antibody that specifically binds to a protein or antigen of choice (in this case the memapsin 2 protein or antigenic subsequence thereof). When the assay is used for monitoring and adjusting the dose of memapsin 2 protein administered to a patient, a standard curve of known concentrations of memapsin 2 protein is prepared, for comparison with test results and for quantitating the amount of memapsin 2 protein in the sample. Typically, the standard curve is generated using the same methodology as is used to detect memapsin 2 protein in the patient sample, e.g., ELISA immunoprecipitation, Western blots, in situ immunohistochemistry, and immunofluorescence assays.

Immunoassays also often use a labeling agent to specifically bind to and label the complex formed by the antibody and antigen. The labeling agent may itself be one of the moieties comprising the antibody/antigen complex. Other proteins capable of specifically binding immunoglobulin constant regions, such as protein A or protein G, may also be used as the label agent. These proteins exhibit a strong non-immunogenic reactivity with immunoglobulin constant regions from a variety of species (see, e.g., Kronval et al., 1973; Akerstrom et al, 1985). The labeling agent can be modified with a detectable moiety, such as biotin, to which another molecule can specifically bind, such as streptavidin. A variety of detectable moieties are well known to those skilled in the art.

Immunoassays for detecting and/or isolating memapsin 2 protein in samples may be either competitive or noncompetitive. An antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Immunoassays in the competitive binding format can also be used for crossreactivity determinations. For example, a polypeptide comprising at least an antigenic subsequence of memapsin 2 protein can be immobilized to a solid support. Proteins are added to the assay that compete for binding of the antisera to the immobilized antigen. The ability of the added proteins to compete for binding of the antisera to the immobilized protein is compared to the ability of memapsin 2 protein to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs.

One of skill in the art will appreciate that it is often desirable to minimize nonspecific binding in immunoassays. Particularly, where the assay involves an antigen or antibody immobilized on a solid substrate it is desirable to minimize the amount of non-specific binding to the substrate. Means of reducing such non-specific binding are well known to those of skill in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied. The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions. Means of detecting labels are well known to those of skill in the art.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VII. Method pf Treatment or Prevention

The antibodies, peptides, polypeptides, polynucleotides, and pharmaceutical compositions described herein can be used in methods for treating, preventing and inhibiting the development of Alzheimer's disease and memapsin 2β-secretase disorders.

The invention further provides methods of reducing memapsin 2β-secretase activity to treat a disease associated with memapsin 2β-secretase activity in a subject in need thereof, the method comprising administering to said subject an effective amount of one or more of the antibodies, peptides, polypeptides, polynucleotides, and pharmaceutical compositions described herein. In some embodiments, the antibody is an antibody which specifically binds to one or more peptides selected from the group consisting of KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTHVPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVEDVATSQDDCYK (SEQ ID NO:7).

The invention provides methods of decreasing levels of β-amyloid peptide in the brain of a subject, said method comprising administering to said subject an effective amount of one or more of the antibodies, peptides, polypeptides, polynucleotides, and pharmaceutical compositions described herein. In some embodiments, the antibody is an antibody which specifically binds to one or more peptides selected from the group consisting of KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTHVPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVEDVATSQDDCYK (SEQ ID NO:7).

The invention also provides methods of reducing the size or number of β-amyloid plaques in the brain of said subject, said method comprising administer to said subject an effective amount of one or more of the antibodies (including polypeptides), polynucleotides, and pharmaceutical compositions described herein. In some embodiments, the antibody is an antibody which specifically binds to one or more peptides selected from the group consisting of KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTHVPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVEDVATSQDDCYK (SEQ ID NO:7).

The invention further provides methods of treating Alzheimer's disease in a patient in need thereof, said method comprising administering to said subject an effective amount of one or more of the antibodies, peptides, polypeptides, polynucleotides, and pharmaceutical compositions described herein. In some embodiments, the antibody is an antibody which specifically binds to one or more peptides selected from the group consisting of KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3), GLAYAEIARPDDSLEPFFDSLVKQTHVPNLFSLQLCGAGFPLNQSEVLAS (SEQ ID NO:4), VEGPFVTLDMEDCGYNIPQTDEST (SEQ ID NO:5), TDEEPEEPGRRGSFVEMVDNLRGKSGQG (SEQ ID NO:6), and MGEVTNQSRFITILPQQYLRPVEDVATSQDDCYK (SEQ ID NO:7).

In some embodiments of any of the above methods, the one or more peptides are selected from the group KMDCKEYNYDKSIVDSGTTNLRLPKK (SEQ ID NO:1), LRLPKKVFEAAVKSIKAA (SEQ ID NO:2), RKGVYVPYTQGKWEGELGTDLVSIPHGPNVTVRANI (SEQ ID NO:3). In some embodiments, the peptide is KMDCKEYNYDKSIVDSGTTNLRLPKK (SEQ ID NO:1). In some embodiments, the peptide is LRLPKKVFEAAVKSI-KAA (SEQ ID NO:2). In some embodiments, the peptide is RKGVYVPYTQGKWEGELGTDLVSIPHGPNVTVRANI (SEQ ID NO:3). In some embodiments, the peptide is GLAYAEIARPDDSLEPFFDSLVKQTHVPNLFSLQLCG-AGFPLNQSEVLAS (SEQ ID NO:4). In some embodiments, the peptide is VEGPFVTLDMEDCGYNIPQTDEST (SEQ ID NO:5). In some embodiments, the peptide is TDEEP-EEPGRRGSFVEMVDNLRGKSGQG (SEQ ID NO:6). In some embodiments, the peptide is MGEVTNQSR-FITILPQQYLRPVEDVATSQDDCYK (SEQ ID NO:7).

Patients, subjects, or individuals include mammals, such as human, bovine, equine, canine, feline, porcine, and ovine animals. The subject is preferably a human, and may or may not be afflicted with disease or presently show symptoms. The methods are applicable to both human therapy and veterinary applications. In some embodiments, the patient or subject is a mammal, such as a primate. In other embodiments, the patient or subject is human.

In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, 1997). Other markers of risk are mutations in the presenilin genes, PS1 and PS2, and ApoE4, family history of AD, hypercholesterolemia or atherosclerosis. In some embodiments, the subject is carries a mutant ApoE4 allele. In some embodiments, the subject is carries a wild-type ApoE4 allele.

Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA (Alzheimer's Disease and Related Disorders Association) criteria. In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by various ways known in the art over time.

VIII. Dosages and Methods of Administration

The invention provides methods of administering the antibodies, peptides, polypeptides, polynucleotides, and pharmaceutical compositions described herein. In some embodiments, the antibodies or peptides can be administered to the mammal by injection (e.g., systemic, intravenous, intraperitoneal, subcutaneous, intramuscular, topically, orally, transdermally, intraportal, intracerebral, intracerebralventricular, by implantation, and intranasal), or by other methods, such as infusion, which ensure its delivery to the bloodstream in an effective form. In some embodiments, the antibodies and peptides may also be administered by isolated perfusion techniques, such as isolated tissue perfusion, to exert local therapeutic effects. In some embodiments, the antibodies are administered intravenously.

In other methods, the proteins, antibodies, and pharmaceutical compositions thereof may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The preparations can also be administered in an aerosol inhaled into the lungs (see, Brigham, 1989) or by direct injection at the site of disease (Culver, 1994).

Effective dosages and schedules for administering the antibody may be determined empirically, and making such determinations is within the skill in the art. Those skilled in the art will understand that the dosage of antibody that must be administered will vary depending on, for example, the mammal that will receive the antibody, the route of administration, the particular type of antibody used and other drugs being administered to the mammal. In some embodiments, the amount of the composition is a therapeutic effective amount. In therapeutic applications, compositions are administered to a patient suffering from a disease in an amount sufficient to cure or at least partially arrest the disease and its complications. Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. In some embodiments, the amount of the composition is a prophylactic amount. The particular dose required for a prophylactic treatment will depend upon the medical condition and history of the mammal, as well as other factors such as age, weight, gender, administration route, efficiency, etc. Such prophylactic treatments may be used, e.g., in a mammal who has previously had AD to prevent a recurrence of the AD, or in a mammal who is suspected of having a significant likelihood of developing AD.

Guidance in selecting appropriate doses for antibody is found in the literature on therapeutic uses of antibodies, e.g., HANDBOOK OF MONOCLONAL ANTIBODIES (1985); Smith et al. (1977). A typical daily dosage of the antibody used alone might range from about 1 μg/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or more, is administered. Antibodies may be administered at lower doses or less frequent at the beginning of the treatment to avoid potential side effect, such as temporary cerebral amyloid angiopathy (CAA).

In some embodiments, a dose of the antibody for intravenous administration would be about 0.1 to 10 mg per patient per day. Dosages of the antibody from 0.1 up to about 100 mg per patient per day may be used, particularly when the drug is administered to a secluded site and not into the blood stream, such as into a body cavity or into a lumen of an organ. Substantially higher dosages are possible in topical administration.

In some individuals, more than one dose may be required. Frequency of administration may be determined and adjusted over the course of therapy. For example, frequency of administration may be determined or adjusted based on the type and severity of the disease to be treated, whether the agent is administered for preventive or therapeutic purposes, previous therapy, the patient's clinical history and response to the agent, and the discretion of the attending physician. Typically the clinician will administer the compound until a dosage is reached that achieves the desired result. Empirical considerations, such as the half-life, generally will contribute to determination of the dosage. For repeated administrations over several days or longer, depending on the condition, the treatment is sustained until a desired suppression of disease symptoms occurs or until sufficient therapeutic levels are achieved. In some cases, sustained continuous release formulations may be appropriate. Various formulations and devices for achieving sustained release are known in the art.

IX. Kits

The invention also provides kits for use in the methods described herein. Kits of the invention include one or more containers comprising any of the compounds (e.g., memapsin 2 peptides or anti-memapsin 2β-secretase antibodies) described herein and instructions for use in accordance with any of the methods of the invention described herein. Generally, these instructions comprise a description of administration of the compound (e.g., memapsin 2 peptides or anti-memapsin 2β-secretase antibodies) according to any of the methods described herein. The kit may further comprise a description of selecting an individual suitable for treatment.

The instructions relating to the use of a compound (e.g., memapsin 2 peptides or anti-memapsin 2β-secretase antibodies) generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a compound (e.g., anti-memapsin 2β-secretase antibodies). The container may further comprise a second pharmaceutically active agent.

X. Examples

The examples, which are intended to be purely exemplary of the invention and should therefore not be considered to limit the invention in any way, also describe and detail aspects and variations of the invention discussed above. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Epitope Mapping of Antibodies Toward Human Promemapsin 2

Effective memapsin 2 (M2) epitopes for immunization were identified as described in this experiment. The polyclonal anti-M2 antibodies were tested for immunoreactivity with 203 overlapping octa-peptides of M2 ecto-domain. The results revealed that several specific epitopes interacted with antibodies in a high binding affinity. The x-ray crystal structure of M2 revealed that the highly antigenic epitopes are exposed on surface loops and secondary structures of M2 around the active-site cleft (and the flap covering the active site) and the APP interaction site.

Peptide Synthesis. The 414 amino acid memapsin 2 amino acid sequence from −21 to 393 of FIG. 1 (43 to 456 of SEQ ID NO:8) was divided to construct 203 sequential overlapping decapeptides, offset by two amino acids, on polystyrene pins. The entire amino acid sequence was synthesized on 3 blocks of 96 pins in an 8×12 format.

Solid Phase Anti-peptide Assay. Procedure was conducted by immersing the pin blocks into microtiter plate wells. Pins were incubated in blocking buffer (1% bovine serum albumin (BSA) in phosphate buffered saline (PBS), pH 7.2) for 1 h at room temperature and then in dilutions of anti-memapsin 2 polyclonal sera or pre-immune sera in diluent (1% BSA and 0.05% Tween in PBS) overnight at 40° C. in humidified containers. Polyclonal anti-memapsin 2 serum was obtained from goats and mice immunized with anti-memapsin 2 (Chang et al., 2007). Pin blocks were washed four times with wash buffer (0.05% Tween in PBS) for 10 min with agitation and then immersed for 1 h at room temperature in affinity purified anti-goat or anti-mouse IgG antibody conjugated to alkaline phosphatase (Sigma Chemical Co., St. Louis, Mo.) diluted 1:1000 in diluent. After washing as above, pins were incubated in para-nitrophenyl phosphate solution at 37° C. for 2 h. Color development was read at 410 nm on an ELISA plate reader.

Regeneration of Pins. After substrate development, pins were incubated in a ~60° C. sonicating water bath containing freshly prepared 1% sodium dodecyl sulfate and 0.1% 2-mercaptoethanol for 1 h. Pins were then rinsed twice in distilled water, pre-heated to 50-60° C., and immersed in boiling methanol for 2 min and air dried.

mAb cell surface memapsin 2 binding. Murine CAD cells were transiently transfected with human memapsin 2 by FuGene (Roch). The transfected CAD cells were labeled with monoclonal antibody (omitted for negative control) followed by Alexa 488 conjugated secondary antibody. The negative control shows the basal level of fluorescence intensity from CAD and the secondary antibody.

Administration of monoclonal antibody to mouse brains. Twelve-month-old AD transgenic mice (Tg2576 from Taconic farm, n=6) were surgically implanted with a catheterized osmotic pump (model #1004, Durect Corp.) filled with monoclonal antibody 1000 or 1003 (19 mg/ml or 15 mg/ml, respectively) or isotype matched irrelevant monoclonal antibody (Vehicle). Infusion devices were placed on the back of the animals and a catheter (30-gauge) was inserted into the right hippocampus at coordinates relative to Bregma of −2.7 mm A/P, 2.5 mm M/L, and −2.5 mm V/D. When the pump was expired after 28 days, animals were subjected to transcardially perfusion followed by brain harvest. The intracellular fraction of the brain homogenates were extracted by 0.1% Triton X100 buffer and Aβ42 concentrations were determined by sandwich ELISA.

Example 2

Epitopes Defined by Common Clusters of Immunoreactivity

Binding of anti-memapsin 2 antibodies to immobilized decapeptides were evaluated. Both mouse and goat anti-memapsin 2 sera displayed immunoreactivity toward various memapsin 2 decapeptides (FIG. 3). Immunoreactive pins were highlighted by number for both goat and mouse anti-memapsin 2 binding in FIG. 3. Pre-immune sera derived from mice did not significantly bind to the decapeptides (FIG. 3).

In particular, strong immunoreactivity was evident toward decapeptides which clustered together in contiguous clusters of overlapping decapeptides (FIGS. 3 and 4). These clusters of immunoreactivity were common to both mouse and goat anti-memapsin 2 sera. Clusters were combined into regions if fewer than 5 amino acids separated the C-terminus of the previous cluster decapeptide with the N-terminus of the following cluster decapeptide (Table 2). These regions were numbered in order of the intensity of the immunoreactive signal in the ELISA (FIG. 3). The two regions of highest intensity were further subdivided to design human memapsin 2 oligopeptides useful as antigens for immunizing animals to test for production of neutralizing antibodies toward memapsin 2 effective to reduce Aβ production. Oligopeptides of length approximately 10-25 amino acids were preferred for optimal immunoreactivity as antigens and limitations of peptide synthesis. Therefore, Region 1 (FIGS. 3 and 4) was subdivided into two sequences for synthesis of oligopeptides representing the major region of common immunoreactivity (peptides named #1-a and 1-b). Region 2 peptide was designated as #2 (FIG. 5).

These peptides are also useful to produce polyclonal and monoclonal antibodies for testing for neutralizing activity in cell culture, and ultimately for production of monoclonal antibody that are further modified to create a suitable pharmaceutical agent for administration to patients suffering from disease resulting from memapsin 2 activity, such as the production of Aβ in Alzheimer's disease.

TABLE 2

Clusters of common immunoreactivity for mouse and goat anti-memapsin 2 sera. Regions are derived from results from solid-phase anti-peptide assay, depicted in FIGS. 3-4

| Region[1] | Decapeptide PIN Number[2] | | Sequential Amino Acid Numbering[3] | | SEQ ID NO: 8 Numbering[4] | | Mature Protease Domain Numbering[5] | |
|---|---|---|---|---|---|---|---|---|
| | Start | End | Start | End | Start | End | Start | End |
| 1 | 118 | 132 | 235 | 272 | 277 | 314 | 214 | 251 |
| 2 | 43 | 56 | 85 | 120 | 127 | 162 | 64 | 99 |
| 3 | 71 | 91 | 141 | 190 | 183 | 232 | 120 | 169 |
| 4 | 196 | 203 | 391 | 414 | 433 | 456 | 370 | 393 |
| 5 | 4 | 13 | 7 | 34 | 49 | 76 | −15 | 13 |
| 6 | 155 | 167 | 309 | 342 | 351 | 384 | 288 | 321 |

[1]Clusters were combined into regions if fewer than 5 amino acids separated the C-terminus of the previous cluster decapeptide with the N-terminus of the following cluster decapeptide.
[2]Number of immunoreactive decapeptide PIN number from beginning to end of immunoreactive region.
[3]Beginning and end of immunoreactive region in sequential numbering (FIG. 2).
[4]Beginning and end of immunoreactive region in numbering scheme according to SEQ ID NO: 8 and FIG. 1.
[5]Beginning and end of immunoreactive region in the scheme of the mature protease domain, numbering from the amino terminus of the homolog pepsin (FIG. 1).

Example 3

Immunization with Memapsin 2 Oligopeptides to Test for Immunogenicity and Neutralizing Activity Memapsin 2 oligopeptides is administered to animals for testing their ability to elicit an immune response that is neutralizing to memapsin 2 activity. Oligopeptides is administered conjugated to additional moieties known to those skilled in the art useful for eliciting an immune response (polylysine backbone, KLH conjugation). Following immune response as detected by measuring the titer of serum of animals immunized with memapsin 2 oligopeptides, the amount of Aβ peptide produced in these animals relative to control animals is measured to test the degree to which antibodies are neutralizing of memapsin 2 activity. Sera from these animals are also used to test the potency of the anti-memapsin 2 oligopeptide antibodies against production of Aβ from cell lines.

Example 4

Immunization with Memapsin 2 Oligopeptides to Test for Monoclonal Antibody Production Memapsin 2 oligopeptides tested for their ability to elicit a memapsin 2 activity-neutralizing immune response are administered to mice or rats for the purpose of producing monoclonal antibodies. The procedures for monoclonal antibody production are known to those skilled in the art. Monoclonal antibodies are tested for their binding affinity to memapsin 2 oligopeptides, to truncated memapsin 2 protein, and for their ability to neutralize memapsin 2 activity in cell lines, assessed by the measure of Aβ production from cells treated with anti-memapsin 2 oligopeptide antibodies in sera of immunized animals, relative to pre-immune sera.

Example 5

Administration of Anti-Memapsin 2 Oligopeptide Antibodies to Reduce Aβ Production The inventors designed two essential memapsin 2 epitopes (FIG. 6) based on results in Example 1. Both Peptide 1a and Peptide 2a are near the active site in the crystal structure of memapsin 2, and are of length suitable for eliciting an immune response. Both peptides were used to conduct a peptide-based active immunization and to clone monoclonal antibodies (mAb).

To demonstrate the efficacy of memapsin 2 oligopeptide-based immunization in animals, the inventors carried out three separate experiments in young Tg2576 mice starting at 5 months of age. Animals then divided into three groups: one is negative control (adjuvant alone), one is positive control using memapsin 2 ectodomain (memapsin $2_{ED}$) immunization as demonstrated by the inventors (Chang et al., 2007), and one experimental group immunized with both peptides 1a and 2a. In order to make the small peptides more antigenic, KLH (Keyhole Limpet Hemocyanin) was conjugated to each of the peptides (kits from Pierce). This was a necessary step for in vivo animal studies to avoid possible immune tolerance due to antigens that are too small, yet sufficient to demonstrate proof of concept. Immunization of memapsin 2 oligopeptides 1a and 2a with Freund's adjuvant (one complete followed by two incomplete) will begin for the first three weeks followed by two doses of weekly injection of peptides only. Monthly injections were made beginning in week 6 and blood samples will be collected weekly to monitor the antibody titers and possibly adjust the frequency of future boosting injections. Observation of adverse side effects were made throughout. According to previous experience (Chang et al., 2007), the titers from the memapsin 2 ectodomain immunization mice using the same adjuvant showed a steady climbing on antibody titers and leveled off after reaching maximal plateau around weeks 12 to 16.

Results from one of the experiments are described below. During the course of 7 months, the anti-memapsin $2_{ED}$ and anti-peptide antibodies as well as the levels of Aβ in the plasma were monitored. After the conclusion of experiments, cognitive performance was assessed and amyloid load in the brain was analyzed. FIG. 7 shows that plasma Aβ of the immunized group started to drop below the control group near the third immunization. This point coincided well with the rise of anti-memapsin 2 antibody titer. The reduction differences were 35 or 20% for memapsin $2_{ED}$ or peptide (i.e., Pep 1+2, corresponding to Peptide 1a and 2a respectively in FIG. 6) immunization, respectively in both A$\beta_{40}$ and A$\beta_{42}$. The ratio of A$\beta_{40}$ over A$\beta_{42}$ in all the experiments remained nearly constant at ~7.5 to 1 (i.e., 7.53+0.17). The inventors concluded that the effect on the reduction of A$\beta_{40}$ over A$\beta_{42}$ from memapsin $2_{ED}$ or peptide 1a and 2a immunization is very similar; therefore, the Aβ ratio remained unchanged.

At the end of the 7-month immunization period, cognitive function was tested for the mice in a reference-memory version of the Morris water maze (MWM), an evaluation of hippocampus-dependent learning. The inventors observed that both memapsin 2 and peptide 1a and 2a immunized Tg2576 animals learned faster during the training sessions as compared with adjuvant-only control mice. The mice were tested for memory bias for the platform location on days 3 and 5. The means of the annulus crossing index (ACI) of the memapsin $2_{ED}$ and peptide 1a and 2a immunized groups showed an improvement over the control (FIG. 8), indicating that the immunized group had better retention. Only the peptide 1a and 2a immunized group showed a statistical significance on ACI improvement (asterisk p<0.05). The results suggest that the memapsin 2 oligopeptide immunization worked at least as good as the whole memapsin 2 ectodomain in mice to improve their cognitive performance as compared to the PBS immunized control mice.

Brain amyloid load and the contents of Aβ were determined (FIG. 9) by immunohistochemical staining for Aβ at the end of the immunization study (mouse age: 12-month-old). One hemisphere of the brains from the control (vehicle), memapsin 2 ectodomain (memapsin 2), or peptide 1a and 2a ("Peptide") immunized mice (n=4) were fixed, sliced, and IHC stained with anti-A$\beta_{39-43}$ mAb (DakoCytomation). Occupied area in percentage and plaque numbers were calculated in the total, cortex, and hippocampus with aid of microscopy and computer software (IPLab v3.65 Eva, Scanalytics). The inventors observed a reduced amyloid load in either the memapsin 2 or peptide 1a and 2a (FIG. 6) immunized mice as compared with the control mice (FIG. 9). The plaque occupied areas were calculated to be reduced to at least 50% or 20% of the control level by the memapsin 2 or peptide 1a and 2a (FIG. 6) immunization. The total plaque numbers were reduced to at least 30% and 15% of the control level by the memapsin 2 or peptide 1a and 2a immunization. Similar percentage reductions were found in the cortical and the hippocampal region of the brain (FIG. 9).

Taken together, these data demonstrate that active immunization of using two of the essential memapsin 2 oligopeptides in the transgenic AD model is more effective than that using the whole memapsin 2 ectodomain on the aspect of amyloid reduction and cognitive rescue.

Example 6

Immunization with Memapsin 2 Oligopeptides for Monoclonal Antibody Production

The inventors designed two essential memapsin 2 epitopes (FIG. 6) based on solid-phase anti-peptide ELISA in Example 1. Nine monoclonal antibodies (mAb) were generated by hybridoma fusion specifically against Peptides 1a or 2a (FIG. 6). The names of those mAb are M2 1000, M2 1001, M2 1002, M2 1003, M2 1004, M2 2000, M2 2001, M2 2002, and M2 2003. The ability of those mAb to bind with the cell surface memapsin 2 molecules, block β-secretase enzymatic activity, and inhibit Aβ production was tested in cultured cells. The inventors observed that anti-peptide 1a and 2a (FIG. 6) mAb 1000 and 1003, respectively, recognize the cell surface memapsin 2 with various capacity and affinity by flow cytometry analysis (FIG. 10).

Example 7

Administration of Anti-Memapsin 2 Oligopeptide Antibodies to Reduce Aβ Production To demonstrate the effectiveness of those anti-memapsin 2 oligopeptide mAb on brain amyloid-β reduction, the inventors carried out experiments in adult Tg2576 mice of 12 months of age. Under anesthesia, animals underwent the intracranial surgery of osmotic pump implantation. The cathetered pump was filled with mAb M2 1000 or M2 1003 specific for peptide 1a and 2a, respectively, and the control pumps were filled with the isotype matched unrelated mAb. The cannula of the pump continuously delivered 0.11 µl of mAb per hour to the right CA1 region of hippocampus. After 28 days of mAb treatment, animals were sacrificed and brains were harvested for immunohistochemical (IHC) staining and homogenation. The former was used to identify the possible adverse immune response triggered by mAb treatment. The results showed no elevated T cell, microglia, and astrocyte activation from IHC staining. The latter was used to determine the content of brain Aβ by ELISA. The intracellular fraction of the brain homogenates were extracted by 0.1% Triton X100 buffer. The results showed in the intracellular fraction of brain homogenate, a reduction of Aβ42 in the range of 30% or 70% for mAb 1000 or 1003, respectively (FIG. 11).

Example 8

Light and Heavy Chain Mab Sequences

The following table shows correspondence for the SEQ ID NOS for the various light and heavy chain protein sequences for each of six monoclonal antibodies that have been sequenced:

| Clone Designation | PROTEIN SEQ ID NO | DNA SEQ ID NO |
|---|---|---|
| 1000L | 9 | 10 |
| 1000H | 11 | 12 |
| 1002L | 13 | 14 |
| 1002H | 15 | 16 |
| 1003L | 17 | 18 |
| 1003H | 19 | 20 |
| 2000L | 21 | 22 |
| 2000H | 23 | 24 |
| 2001L | 25 | 26 |
| 2003L | 27 | 28 |
| 2003H | 29 | 30 |
| 1001L | 31 | |
| 1001H | 32 | |
| 1004L | 33 | |
| 1004H | 34 | |
| 2002L | 35 | |
| 2002H | 36 | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

| | Sequence Listing | |
|---|---|---|
| SEQ ID 1 Region 1a | KMDCKEYNYDKSIVDSGTTNLRLPKK | |
| SEQ ID 2 Region 1b | LRLPKKVFEAAVKSIKAA | |
| SEQ ID 3 Region 2 | RKGVYVPYTQGKWEGELGTDLVSIPHGPNVTVRANI | |
| SEQ ID 4 Region 3 | GLAYAEIARPDDSLEPFFDSLVKQTHVPNLFSLQLCGAGFPLNQSEVLAS | |
| SEQ ID 5 Region 4 | VEGPFVTLDMEDCGYNIPQTDEST | |
| SEQ ID 6 Region 5 | TDEEPEEPGRRGSFVEMVDNLRGKSGQG | |
| SEQ ID 7 Region 6 | MGEVTNQSFRITILPQQYLRPVEDVATSQDDCYK | |

| | Sequence Listing |
|---|---|
| SEQ ID 8 | MASMTGGQQMGRGSMAGVLPAHGTQHGIRLPLRSGLGGAPLGLRLPRETDEEPEEPGRRGSFVEMVDNLRGKSGQGYYVEMTVGSPPQTLNILVDTGSSNFAVGAAPHPFLHRYYQRQLSSTYRDLRKGVYVPYTQGKWEGELGTDLVSIPHGPNVTVRANIAAITESDKFFINGSNWEGILGLAYAEIARPDDSLEPFFDSLVKQTHVPNLFSLQLCGAGFPLNQSEVLASVGGSMIIGGIDHSLYTGSLWYTPIRREWYYEVIIVRVEINGQDLKMDCKEYNYDKSIVDSGTTNLRLPKKVFEAAVKSIKAASSTEKFPDGFWLGEQLVCWQAGTTPWNIFPVISLYLMGEVTNQSFRITILPQQYLRPVEDVATSQDDCYKFAISQSSTGTVMGAVIMEGFYVVFDRARKRIGFAVSACHVHDEFRTAAVEGPFVTLDMEDCGYNIPQTDEST |

XI. References

The following references, to the extent that they provide exemplary procedural or other details supplementary to those set forth herein, are specifically incorporated herein by reference.

Adams et al., *Cancer Res.*, 53:4026, 1993.
Akerstrom et al, *J. Immunol.*, 135:2589-2542, 1985.
Al-lazikani et al., *J. Molec. Biol.*, 273:927-948, 1997.
Altschul et al., *J. Mol. Biol.*, 215:403-410, 1990.
Altschul et al., *Nuc. Acids Res.*, 25:3389-3402, 1977.
Balint et al., *Gene*, 137(1):109-18, 1993.
Barbas et al., *Proc Nat. Acad. Sci. USA*, 91:3809-3813, 1994.
*Basic and Clinical Immunology*, Stites & Terr (Eds), 7th Ed., 1991.
Bird et al., *Science*, 242:423-426, 1988.
Boemer et al., *J. Immunol.*, 147(1):86-95, 1991.
Boyd et al., *Mol. Immunol.*, 32:1311-1318, 1996.
Brigham, et al., *Am. J. Sci.*, 298(4):278-281, 1989.
Capell et al., *J. Biol. Chem.*, 275:30849-30854, 2000.
Chang et al., *FASEB J*, 21:3184-3196, 2007.
Cole et al., *Monoclonal Antibodies and Cancer Therapy*, 77, 1985.
Coligan, *Current Protocols Immunology*, 1991.
Culver, *Human Gene Therapy*, MaryAnn Liebert, Inc., Publishers, NY, 70-71, 1994.
*Enzyme Immunoassay*, Maggio (Ed.), 1980.
EP 03089
*Epitope Mapping Protocols in Methods in Molecular Biology*, Vol. 66, Morris (Ed.), 1996.
Ermolieff et al., *Biochemistry*, 39(40):12450-12456, 2000.
Fishwild et al., *Nature Biotechnology*, 14:845-51, 1996.
*Fundamental Immunology* (Paul Ed.), 3rd Ed. 1993.
Goding, *Monoclonal Antibodies: Principles and Practice* (2nd Ed.), 1986.
Goodman & Gillman, *The Pharmacological Basis of Therapeutics*, Hardman et al (Eds.), 1996.
*Handbook of Monoclonal Antibodies*, Ferrone et al. (Eds.), Noges Publications, Park Ridge, N.J., 22:303-357, 1985.
Hardy, *Trends Neurosci.*, 20:154-9, 1997.
Hawkins et al, *J. Mol. Biol.*, 226:889-896, 1992.
He et al., *FEBS Letters*, 524:183-187, 2002.
Henikoff & Henikoff, *Proc. Natl. Acad. Sci. USA*, 89:10915, 1989.
Holliger et al., *Proc. Natl. Acad Sci. USA*, 90:6444-6448, 1993.
Hong et al., *Science*, 290:150-153, 2000.
Hoogenboom and Winter, *J. Mol. Biol.*, 227:381, 1991.
Hu et al., *Cancer Res.*, 56:3055, 1996.

Huse et al., *Science*, 246:1275-1281, 1989.
Hussain et al., *Mol. Cell. Neurosci.*, 14:419-427, 1999.
Jackson et al., *J. Immunol.*, 154(7):3310-9, 1995.
Jefferis and Lund, *Chem. Immunol.*, 65:111-128, 1997.
Kabat et al., *Sequences of Proteins of Immunological Interest*, 5th Ed., 1991.
Karlin & Altschul, *Proc. Natl. Acad. Sci. USA*, 90:5873-5787, 1993.
Kohler & Milstein, *Nature*, 256:495-497, 1975.
Kostelny et al. *J. Immunol.*, 148:1547, 1992.
Kronval et al., *J. Immunol.*, 111:1401-1406, 1973.
Kuby, *J. Immunology*, 3rd Ed., W.H. Freeman & Co., NY, 1998.
Lin et al., *Proc. Natl. Acad. Sci. USA*, 97:1456-1460, 2000.
Lonberg & Huszar, *Intern. Rev. Immunol.*, 13:65-93, 1995.
Lonberg et al., *Nature*, 368:856-859, 1994.
Marks et al., *Bio/Technology*, 10:779-783, 1992.
Marks et al., *J. Mol. Biol.*, 222:581, 1991.
McCafferty et al., *Nature*, 348:552-554, 1990.
McCartney, et al. *Protein Eng.*, 8:301, 1995.
*Methods in Cell Biology: Antibodies in Cell Biology*, 37, Asai (Ed.), 1993.
Millstein and Cuello, *Nature*, 305:537-539, 1983.
Morrison, *Nature*, 368:812-13, 1994.
Mosmann and Coffman, *Ann. Rev. Immunol.*, 7:145-173, 1989.
Neuberger, *Nature Biotechnology*, 14:826, 1996.
Oddo et al., *J. Biol. Chem.*, 281:1599-1604, 2006.
Pack and Pluckthun, *Biochemistry*, 31:1579, 1992.
*PCR: The Polymerase Chain Reaction*, Mullis et al. (Eds.), Birkauswer Press, Boston, 1994.
PCT Appln WO2004/058184
PCT Appln. WO 2007/021886
PCT Appln. WO 87/04462
PCT Appln. WO 91/00360
PCT Appln. WO 92/200373
PCT Appln. WO 94/00153
PCT Appln. WO 94/04690
PCT Appln. WO 95/17209
PCT Appln. WO 99/58572
*Pierce Catalog and Handbook*, Pierce Chemical Co., Rockford, Ill., 1994-1995.
Poljak et al., *Structure*, 2:1121-1123, 1994.
Remington's Pharmaceutical Sciences, 15th ed., 33:624-652, Mack Publishing Company, Easton, Pa., 1980.
Remington's Pharmaceutical Sciences, 18th Ed., Mack Printing Company, 1289-1329, 1990.
Remington's Pharmaceutical Sciences, 20th Ed., Mack Printing Company, 2000.
Sambrook et al., In: *Molecular cloning*, Cold Spring Harbor Laboratory Press, Cold Spring Harbor, N.Y., 1989.
Schier et al., *Gene*, 169:147-155, 1995.
Selkoe and Schenk, *Annu. Rev. Pharmacol. Toxicol.*, 43:545-584, 2003.
Selkoe, *Nature*, 399:A23-A31, 1999.
Sheets et al., *Proc. Natl. Acad. Sci. USA*, 95:6157-6162, 1998.
Smith et al., *Antibodies in Human Diagnosis and Therapy*, Haber et al. (Eds.), Raven Press, NY, 365-389, 1977.
Suresh et al., *Methods in Enzymology*, 121:210, 1986.
Turner et al., *Biochemistry*, 40:10001-10006, 2001.
U.S. Pat. No. 4,676,980
U.S. Pat. No. 4,683,195
U.S. Pat. No. 4,683,202
U.S. Pat. No. 4,754,065
U.S. Pat. No. 4,800,159
U.S. Pat. No. 4,816,567
U.S. Pat. No. 5,225,539
U.S. Pat. No. 5,530,101
U.S. Pat. No. 5,545,806
U.S. Pat. No. 5,545,807
U.S. Pat. No. 5,569,825
U.S. Pat. No. 5,585,089
U.S. Pat. No. 5,625,126
U.S. Pat. No. 5,633,425
U.S. Pat. No. 5,661,016
U.S. Pat. No. 5,693,761
U.S. Pat. No. 5,693,762
U.S. Pat. No. 5,750,373
U.S. Pat. No. 5,807,715
U.S. Pat. No. 5,866,692
U.S. Pat. No. 5,997,867
U.S. Pat. No. 6,180,370
U.S. Pat. No. 6,331,415
U.S. Pat. No. 6,545,127
U.S. Pat. No. 6,548,640
Umana et al., *Mature Biotech.*, 17:176-180, 1999.
Vassar et al., *Science*, 286:735-741, 1999.
Vaughan et al., *Nature Biotechnology*, 14:309-314, 1996.
Ward et al., *Nature*, 341:544-546, 1989.
Wittwe and Howard, *Biochem.*, 29:4175-4180, 1990.
Wolfe, *Curr. Topics Med. Chem.*, 2(4):371-383, 2002.
Wright and Morrison, *TibTECH*, 15:26-32, 1997.
Wyss and Wagner, *Current Opin. Biotech.*, 7:409-416, 1996.
Yan et al., *Nature*, 402:533-537, 1999.
Yelton et al., *J. Immunol.*, 155:1994-2004, 1995.
Zhu et al. *Protein Sci.*, 6:781, 1997.

What is claimed:

1. An isolated monoclonal antibody or antigen-binding fragment thereof which specifically binds to the sequence KMDCKEYNYDKSIVDSGTTNLRLPKK (SEQ ID NO: 1).

2. The monoclonal antibody or fragment thereof of claim 1, wherein the monoclonal antibody is a chimeric antibody, humanized antibody, or human antibody.

3. The monoclonal antibody or fragment thereof of claim 1, wherein the antigen-binding fragment comprises Fab, Fab', $F(ab')_2$ or Fv fragment.

4. The monoclonal antibody of claim 1, wherein the monoclonal antibody is an $IgG_1$ or $IgG_{2b}$ isotype antibody.

5. The monoclonal antibody or fragment thereof of claim 1, wherein the monoclonal antibody comprises light and heavy chain sequences selected from the following pairs:
SEQ ID NOS: 9 and 11;
SEQ ID NOS: 13 and 15;
SEQ ID NOS: 31 and 32; and
SEQ ID NOS: 33 and 34.

6. A cell line expressing the antibody of claim 1.

7. The cell line of claim 6, wherein the monoclonal antibody is a chimeric antibody, humanized antibody, or human antibody.

8. The cell line of claim 6, wherein the monoclonal antibody is an $IgG_1$ or $IgG_{2b}$ isotype antibody.

9. The cell line of claim 6, wherein the monoclonal antibody comprises light and heavy chain sequences selected from the follow pairs:
SEQ ID NOS: 9 and 11;
SEQ ID NOS: 13 and 15;
SEQ ID NOS: 31 and 32; and
SEQ ID NOS: 33 and 34.

* * * * *